United States Patent
Kraatz et al.

(10) Patent No.: US 6,410,581 B1
(45) Date of Patent: Jun. 25, 2002

(54) DISUBSTITUTED BIPHENYLOXAZOLINES

(75) Inventors: Udo Kraatz, Leverkusen; Wolfgang Krämer, Burscheid; Albrecht Marhold, Leverkusen; Christoph Erdelen, Leichlingen; Ulrike Wachendorff-Neumann, Neuwied; Andreas Turberg, Haan; Norbert Mencke, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/367,981
(22) PCT Filed: Feb. 20, 1998
(86) PCT No.: PCT/EP98/00973
§ 371 (c)(1), (2), (4) Date: Aug. 23, 1999
(87) PCT Pub. No.: WO98/39310
PCT Pub. Date: Sep. 11, 1998

(30) Foreign Application Priority Data

Mar. 5, 1997 (DE) ........................................ 197 08 923
May 2, 1997 (DE) ........................................ 197 18 522
Dec. 22, 1997 (DE) ........................................ 197 57 223

(51) Int. Cl.$^7$ ........................ A01N 43/76; C07D 263/12
(52) U.S. Cl. ........................................ 514/374; 548/239
(58) Field of Search ........................... 548/239; 514/374

(56) References Cited

U.S. PATENT DOCUMENTS

| 3,673,237 A | 6/1972 | Janiak .................... 260/468 P |
| 5,354,905 A | 10/1994 | Sato et al. ................... 564/186 |
| 5,969,147 A | * 10/1999 | Lantzsch et al. ............. 548/237 |

FOREIGN PATENT DOCUMENTS

| EP | 0 432 661 | 6/1991 |
| EP | 0 645 085 | 3/1995 |
| EP | 0 696 584 | 2/1996 |
| EP | 696584 | * 2/1996 |
| WO | 96/18619 | 6/1996 |
| WO | 96/22283 | 7/1996 |

OTHER PUBLICATIONS

Cram and Hammond, "Organic Chemistry", McGraw Hill Book Co., NY (1964) 2nd ed pp 565–567.*
J. Amer. Chem. Soc., 61, Jun. 1939, p. 1447–1449, Hazlet et al, The Bromination of 4–Phenylphenyl Benzoate.
J. Amer. Chem. Soc., 61, Nov. 1939, pp. 3037–3039, Hazlet et al, The Bromination of 4–Phenylphenyl Acetate.
J. Amer. Chem. Soc., 56, Jan. 1934, pp. 202–204, Colbert et al, Chlorine Derivatives of 4–Hydroxydiphenyl.
J. Amer. Chem. Soc., 64, Sep. 1942, pp. 2219–2221, Savoy et al, The Halogenation of Certain Esters in the Biphenyl Series. I. The Chlorination of 4–Phenylphenyl Acetate.
J. Amer. Chem. Soc., 89, (month unavailable) 1967, pp. 2711–2719, Brown et al, Mass Spectrometry in Structural and Stereochemical Problems. CXXX. A Study of Electron Impact Induced Migratory Aptitudes.
J. Indian Chem. Soc., 12, (month unavailable) 1935, pp. 410–417, Nripendranath Chatterjee, Studies in Diphenyl Series. Part I. Synthesis of Unsymmetrical Derivatives Diphenyl.
J. Amer. Chem. Soc., 80, Jul. 5, 1958, pp. 3271–3277, White et al, The ortho–Claisen Rearrangement. I. The Effect of Substituents on the Rearrangement of Allyl p–X–Phenyl Ethers.
J. Org. Chem. 29, (month unavailable) 1964, pp. 3014–3021, Nickon et al, Out–of–Ring Claisen Rearrangements.
J. Amer. Soc., 56, (month unavailable) 1934, pp. 202–204, Colbert et al, Chlorine Derivatives of 4–Hydroxydiphenyl.
J. Org. Chem., 29, (month unavailable) 1964, Fields et al, Preparation of Acetoxybenzy Bromides, pp. 2640–2647.
Organic Reactions, vol. II, The Claisen Rearrangement, D. S. Tarbell, (month unavailable) 1944, pp. 1–48.
J. Org. Chem., Jul. 27, 1962, pp. 2671–2672, Hazlet et al, The Bromination of Ethyl 4–Phenylphenyl Carbonate.

* cited by examiner

*Primary Examiner*—Patricia L. Morris
(74) *Attorney, Agent, or Firm*—Joseph C. Gil; Raymond J. Harmuth

(57) ABSTRACT

The present invention relates to novel biphenyloxazolines of the formula (I)

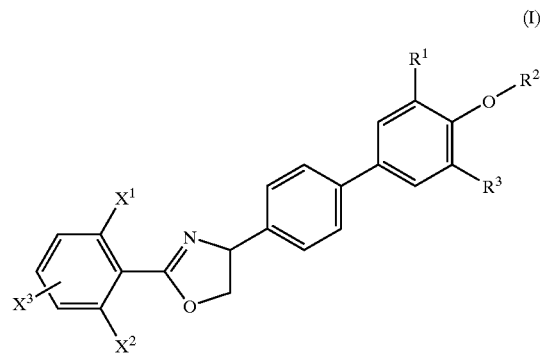

in which
 $X^1$, $X^2$, $X^3$, $R^1$, $R^2$ and $R^3$ are each as defined in the description,
to processes for their preparation and to the use of the biphenyloxazolines for controlling animal pests.

12 Claims, No Drawings

DISUBSTITUTED BIPHENYLOXAZOLINES

TECHNICAL FIELD OF THE INVENTION

The invention relates to novel biphenyloxazolines, to processes for their preparation and to the use of the biphenyloxazolines for controlling animal pests.

BACKGROUND OF THE INVENTION

It is known that certain biphenyloxazolines have insecticidal and acaricidal activity, for example the compounds 2-(2,6-difluorophenyl)-4-(3'-chloro-4'-(1,1,2,2-tetrafluoroethoxy)-biphenyl-4)-2-oxazoline (EP-A-0 696 584) and 2-(2,6-difluorophenyl)-4-(3'-chloro-4'-methylbiphenyl-4)-2-oxazoline (EP-A-0 432 661).

However, the efficacy and/or the duration of action of these known compounds, in particular against certain organisms or at low application concentrations, is not entirely satisfactory in all areas of use.

DETAILED DESCRIPTION OF THE INVENTION

This invention, accordingly, provides novel disubstituted biphenyloxazolines of the formula (I)

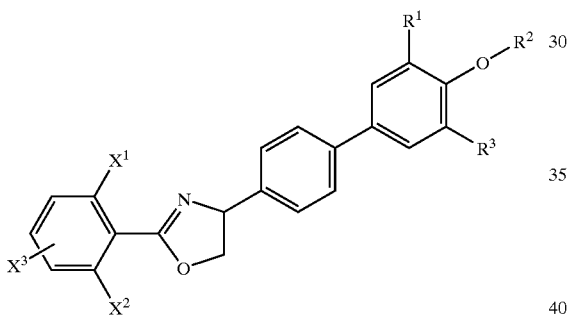

in which
- $X^1$ represents hydrogen, halogen, alkyl, alkoxy or alkylthio,
- $X^2$ represents halogen, alkyl, alkoxy or alkylthio,
- $X^3$ represents hydrogen, halogen, alkyl, alkoxy or alkylthio, in particular hydrogen,
- $R^1$ represents hydrogen, halogen, alkyl or —$CH_2$—$CR^4$=$CH_2$,
- $R^2$ represents alkyl, hydroxyalkyl, respectively optionally substituted alkenyl, alkinyl, cycloalkyl, cycloalkenyl, cycloalkylalkyl, cycloalkenylalkyl, phenyl-alkyl, naphthylalkyl or tetrahydronaphthylalkyl and
- $R^3$ represents hydrogen, alkyl, halogen or the radical —$CH_2$—$CR^4$=$CH_2$, where $R^1$ and $R^3$ do not simultaneously represent hydrogen, and
- $R^4$ represents hydrogen or respectively optionally substituted alkyl or aryl.

Owing to one or more chiral centres, the compounds of the formula (I) are generally obtained as stereoisomer mixtures. They can be employed both in the form of their diastereomer mixtures and as pure diastereomers or enantiomers.

Furthermore, it has been found that the novel compounds of the formula (I) are obtained when A) compounds of the formula (II)

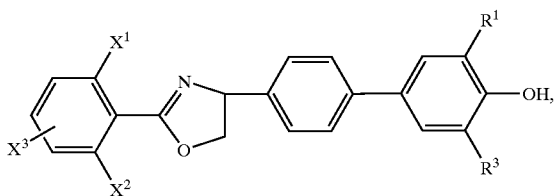

in which
$X^1$, $X^2$, $X^3$, $R^3$ and $R^1$ are each as defined above, $R^3$=$R^1$=hydrogen being possible here if $R^2$ represents allyl and step B) is carried out,
are reacted with compounds of the formula (III)

$$Z-R^2 \quad (III),$$

in which
$R^2$ is as defined above and
Z represents a leaving group,
if appropriate in the presence of a diluent and if appropriate in the presence of a base and B) if appropriate, the compounds of the formula (IV) obtained in this manner for $R^2$=—$CH_2$—$CR^4$=$CH_2$ and $R^3$=H

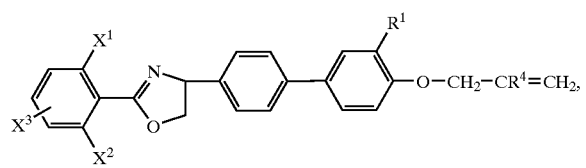

in which
$R^1$, $R^4$, $X^1$, $X^2$ and $X^3$ are each as defined above, are subsequently subjected to a Claisen rearrangement and C) if appropriate, the resulting compounds of the formula (V)

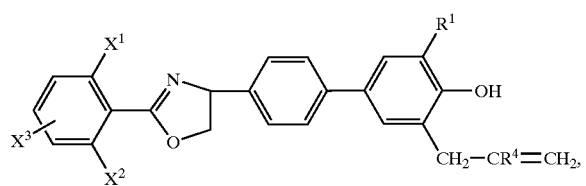

in which
$X^1$, $X^2$, $X^3$, $R^1$ and $R^4$ are each as defined above,
are subsequently reacted with compounds of the formula (III)

$$Z-R^2 \quad (III),$$

in which
$R^2$ and Z are each as defined above,
if appropriate in the presence of a diluent and if appropriate in the presence of a base and, if appropriate, steps B) and C) are then repeated for $R^2=$—$CH_2$—$CR^4=CH_2$ and $R^1=H$, affording compounds of formula (Va)

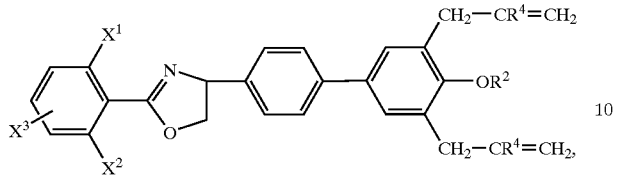
(Va)

in which
$X^1$, $X^2$, $X^3$, $R^2$ and $R^4$ are each as defined above,
and the radicals $R^4$ may be identical or different.

Furthermore, it has been found that the novel compounds of the formula (I) are highly suitable for controlling animal pests, in particular insects, arachnids and nematodes which are encountered in agriculture, in forests, in the protection of materials and of stored goods and in the hygiene sector.

The formula (I) provides a general definition of the compounds according to the invention.

Preferred substituents or ranges of the radicals listed in the formulae mentioned hereinabove and hereinbelow are illustrated below.

$X^1$ preferably represents hydrogen, fluorine, chlorine, bromine, iodine, $C_1$–$C_6$-alkyl, $C_1$–$C_6$-alkoxy or $C_1$–$C_6$-alkylthio.

$X^2$ preferably represents fluorine, chlorine, bromine, iodine, $C_1$–$C_6$-alkyl, $C_1$–$C_6$-alkoxy or $C_1$–$C_6$-alkylthio.

$X^3$ preferably represents hydrogen, fluorine, chlorine, $C_1$–$C_6$-alkyl or $C_1$–$C_6$-alkoxy, in particular hydrogen.

$R^1$ preferably represents hydrogen, fluorine, chlorine, bromine, $C_1$–$C_6$-alkyl or —$CH_2$—$CR^4=CH_2$.

$R^2$ preferably represents $C_1$–$C_8$-alkyl, $C_1$–$C_6$-hydroxyalkyl, $C_3$–$C_{10}$-alkenyl, $C_3$–$C_{12}$-alkinyl, preferably represents respectively optionally halogen- or $C_1$–$C_4$-alkyl-substituted $C_3$–$C_6$-cycloalkyl or $C_4$–$C_6$-cycloalkenyl, preferably represents optionally halogen-, $C_1$–$C_4$-alkyl-, $C_2$–$C_4$-alkenyl-, $C_2$–$C_4$-halogenoalkenyl-, phenyl-, halogenophenyl-, styryl- or halogenostyryl-substituted $C_3$–$C_6$-cycloalkyl-$C_1$–$C_4$-alkyl, preferably represents optionally halogen- or $C_1$–$C_4$-alkyl-substituted $C_4$–$C_8$-cycloalkenyl-$C_1$–$C_2$-alkyl, or preferably represents phenyl-$C_1$–$C_4$-alkyl which is optionally mono- to tetrasubstituted by identical or different substituents from the group consisting of nitro, halogen, $C_1$–$C_{12}$-alkyl, $C_1$–$C_{12}$-halogenoalkyl, $C_1$–$C_{12}$-alkylthio, $C_1$–$C_{12}$-halogenoalkylthio, $C_1$–$C_{12}$-alkoxy and $C_1$–$C_{12}$-halogenoalkoxy, preferably represents naphthyl-$C_1$–$C_3$-alkyl or tetrahydronaphthyl-$C_1$–$C_3$-alkyl.

$R^3$ preferably represents hydrogen, $C_1$–$C_4$-alkyl, fluorine, chlorine, bromine or represents —$CH_2$—$CR^4=CH_2$, where $R^1$ and $R^3$ do not simultaneously represent hydrogen.

$R^4$ preferably represents hydrogen, $C_1$–$C_{12}$-alkyl or preferably represents phenyl which is optionally mono- to tetrasubstituted by identical or different substituents from the group consisting of halogen, $C_1$–$C_{12}$-alkyl, $C_1$–$C_{12}$-halogenoalkyl, $C_1$–$C_{12}$-alkoxy and $C_1$–$C_{12}$-halogenoalkoxy.

$X^1$ particularly preferably represents hydrogen, fluorine or chlorine.

$X^2$ particularly preferably represents fluorine, chlorine, bromine, iodine, $C_1$–$C_3$-alkyl or $C_1$–$C_3$-alkoxy.

$X^3$ particularly preferably represents hydrogen, fluorine, chlorine, $C_1$–$C_3$-alkyl or $C_1$–$C_3$-alkoxy, in particular hydrogen.

$R^1$ particularly preferably represents hydrogen, fluorine, chlorine, bromine, $C_1$–$C_4$-alkyl or —$CH_2$—$CR^4=CH_2$.

$R^2$ particularly preferably represents $C_1$–$C_6$-alkyl, $C_1$–$C_4$-hydroxyalkyl, $C_3$–$C_{10}$-alkenyl, $C_3$–$C_5$-alkinyl, particularly preferably represents respectively optionally halogen- or $C_1$–$C_4$-alkyl-substituted cyclohexyl or $C_4$–$C_6$-cycloalkenyl, particularly preferably represents optionally halogen-, $C_1$–$C_4$-alkyl-, $C_2$–$C_4$-alkenyl-, $C_2$–$C_3$-halogenoalkenyl-, phenyl-, halogenophenyl-, styryl- or halogenostyryl-substituted $C_3$–$C_6$-cycloalkyl-$C_1$–$C_4$-alkyl, particularly preferably represents optionally halogen-substituted $C_4$–$C_6$-cycloalkenylmethyl or particularly preferably represents benzyl which is optionally mono- or disubstituted by identical or different substituents from the group consisting of nitro, halogen, $C_1$–$C_4$-alkyl, $C_1$–$C_4$-halogenoalkyl, $C_1$–$C_4$-alkylthio, $C_1$–$C_4$-halogenoalkylthio, $C_1$–$C_4$-alkoxy and $C_1$–$C_4$-halogenoalkoxy, particularly preferably represents naphthylmethyl or tetrahydronaphthyl-methyl.

$R^3$ particularly preferably represents hydrogen, $C_1$–$C_3$-alkyl, chlorine, bromine or —$CH_2$—$CR^4=CH_2$, where $R^1$ and $R^3$ do not simultaneously represent hydrogen.

$R^4$ particularly preferably represents hydrogen, $C_1$–$C_4$-alkyl or particularly preferably represents phenyl which is optionally mono- or disubstituted by identical or different substituents from the group consisting of fluorine, chlorine, bromine, $C_1$–$C_4$-alkyl, $C_1$–$C_4$-halogenoalkyl and $C_1$–$C_4$-halogenoalkoxy.

In the preferred and particularly preferred radical definitions, halogen represents in particular fluorine, chlorine and bromine.

$X^1$ very particularly preferably represents hydrogen, fluorine or chlorine.

$X^2$ very particularly preferably represents fluorine, chlorine, bromine, iodine, methyl or methoxy.

$X^3$ very particularly preferably represents hydrogen, fluorine, chlorine or methyl, in particular hydrogen.

$R^1$ very particularly preferably represents hydrogen, fluorine, chlorine, bromine, methyl, ethyl, n- or i-propyl or represents allyl.

$R^2$ very particularly preferably represents methyl, ethyl, n- or i-propyl, n-butyl, i-butyl, s-butyl, n-pentyl, n-hexyl, hydroxyethyl, hydroxypropyl, hydroxybutyl, very particularly preferably represents —$CH_2$—$CH=CH_2$, —$CH_2$—$C(CH_3)=CH_2$, —$CH_2$—$C\equiv CH$ or —$CH(CH_3)C\equiv CH$, very particularly preferably represents one of the cycloalkylalkyl groupings:

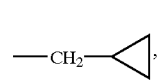 , 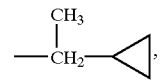 ,

-continued

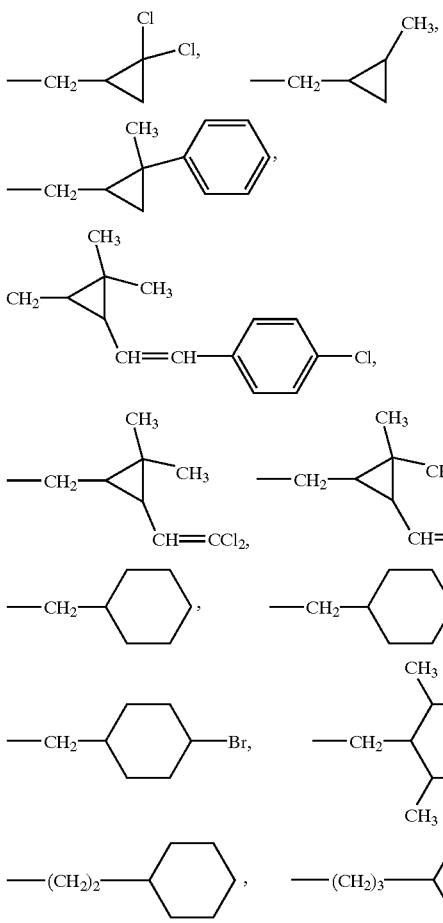

very particularly preferably represents,

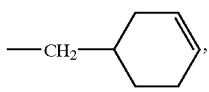

very particularly preferably represents

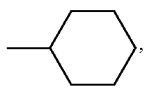

very particularly preferably represents one of the radicals below:

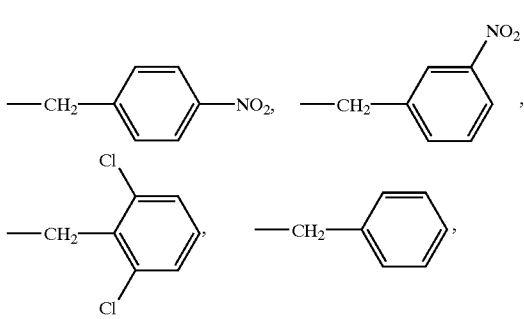

-continued

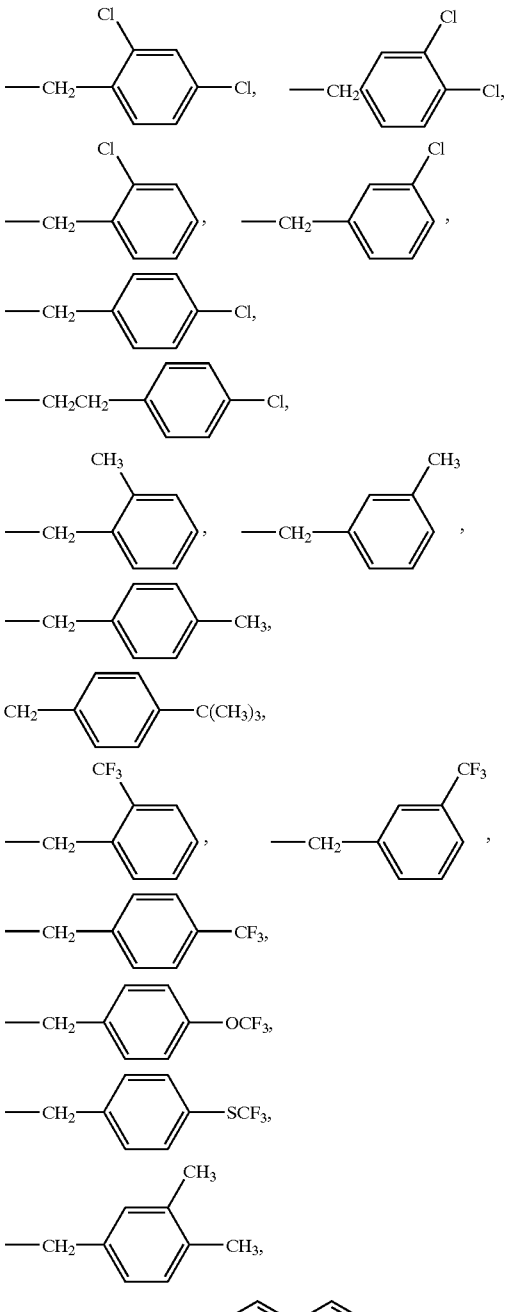

$R^3$ very particularly preferably represents hydrogen, chlorine, bromine, methyl or —CH$_2$—CH=CH$_2$, in particular hydrogen, chlorine or —CH$_2$—CH=CH$_2$, where $R^1$ and $R^3$ do not simultaneously represent hydrogen.

Preference is furthermore given to compounds of the formula (Ia)

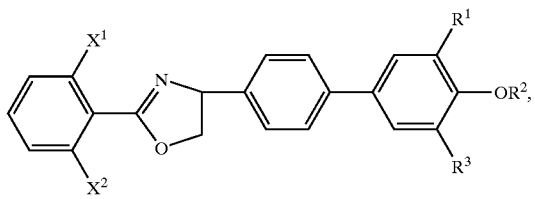

(Ia)

in which
R$^1$, R$^2$, R$^3$, X$^1$ and X$^2$ each have the abovementioned general, preferred, particularly preferred or very particularly preferred meanings.

In each case, R$^1$ and R$^3$ may not simultaneously represent hydrogen.

A preferred group of compounds are also those compounds of the formula (Ib)

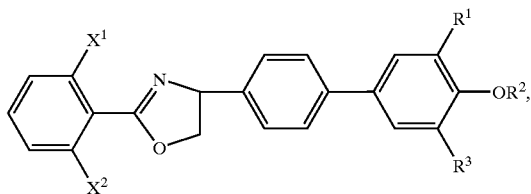

(Ib)

in which
X$^1$ represents hydrogen or fluorine,
X$^2$ represents fluorine, chlorine, bromine or methyl,
R$^1$ represents chlorine, methyl, ethyl, n- or i-propyl or allyl and
R$^2$ has the abovementioned general, preferred, particularly preferred and very particularly preferred meanings and most preferably represents benzyl which may be substituted as mentioned above,
R$^3$ represents hydrogen, chlorine, bromine, methyl or allyl, in particular hydrogen, chlorine or allyl.

Within these groups, preference is given to compounds in which R$^3$ represents hydrogen.

The hydrocarbon radicals, such as alkyl or alkenyl, mentioned above in the definition of the compounds according to the invention are—also in combination with hetero atoms, such as in alkoxy—in each case straight-chain or branched as far as this is possible.

The abovementioned general or preferred definitions of radicals or illustrations can be combined with one another as desired, that is to say combinations between the respective ranges and preferred ranges are also possible. They apply both to the end products and, correspondingly, to the precursors and intermediates.

Preference according to the invention is given to those compounds of the formula (I) which contain a combination of the definitions given above as being preferred (preferable).

Particular preference according to the invention is given to those compounds of the formula (I) which contain a combination of the definitions given above as being particularly preferred.

Very particular preference according to the invention is given to those compounds of the formula (I) which contain a combination of the definitions given above as being very particularly preferred.

Using, for example, 2-(2,6-difluorophenyl)-4-(4'-hydroxy-3'-n-propylbiphenyl-4)-2-oxazoline and isopropyl bromide as starting materials, the course of step A) of the process according to the invention can be represented by the following equation:

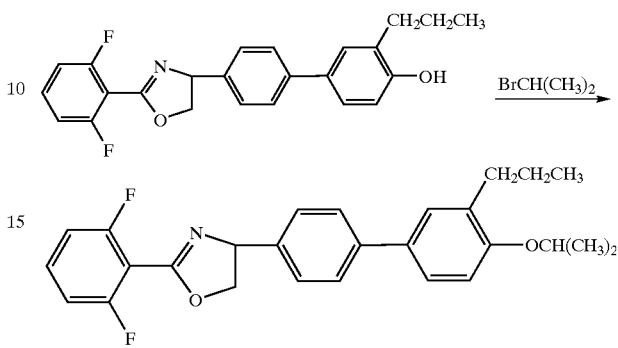

Using, for example, 2-(2,6-difluorophenyl)-4-(4'-allyloxy-3'-chlorobiphenyl-4)-2-oxazoline as starting material, the course of step B) of the process according to the invention can be represented by the following equation:

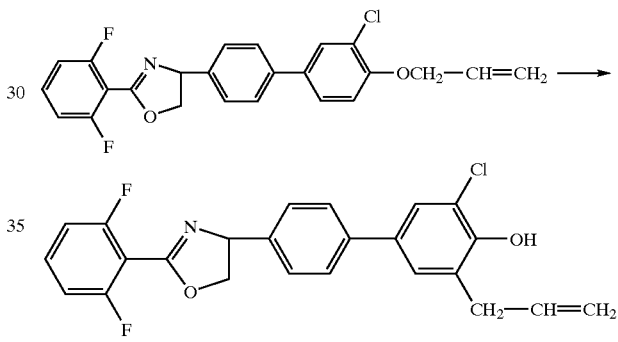

Using, for example, 2-(2,6-difluorophenyl)-4-(3'-allyl-5'-chloro-4'-hydroxybiphenyl-4)-2-oxazoline and benzyl bromide as starting materials, the course of step C) of the process according to the invention can be represented by the following equation:

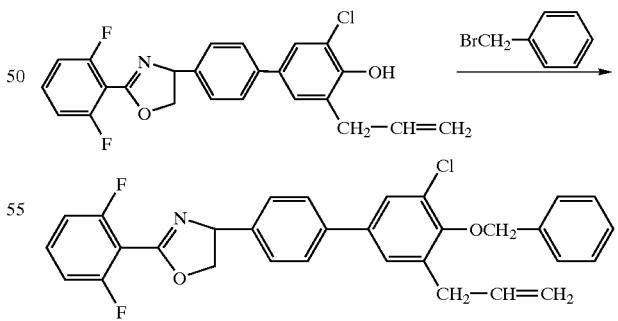

The compounds of the formula (II) required as starting materials for step A) of the process according to the invention are novel if R$^3$ and R$^1$ do not simultaneously represent hydrogen.

The compounds of the formula (II) are obtained, for example, when compounds of the formula (VI)

(VI)

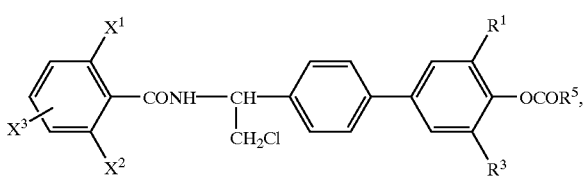

in which

X¹, X², X³, R¹ and R³ are each as defined above and R⁵ represents alkyl (for example methyl), aryl (for example phenyl) or alkoxy (for example methoxy or ethoxy), are cyclized in the presence of a base, if appropriate in the presence of a catalyst and if appropriate in the presence of a diluent, and the acyl group is subsequently cleaved off (process D).

Using, for example, 2,6-difluoro-N-[2-chloro-1-(4-(4-acetoxy-3-n-propyl-phenyl)phenyl)ethyl]-benzamide as starting material, the course of the process D) for preparing compounds of the formula (II) can be represented by the following equation:

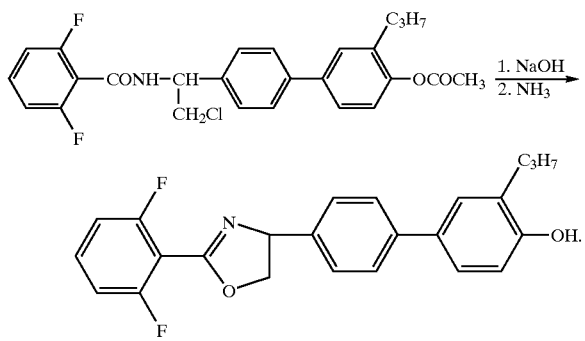

Suitable diluents for process D) are all inert organic solvents. If appropriate, they can be employed as a mixture with water. Preference is given to using hydrocarbons such as toluene, xylene, tetralin, hexane, cyclohexane, halogenated hydrocarbons such as methylene chloride, chloroform, chlorobenzene, o-dichlorobenzene, alcohols such as methanol, ethanol, glycol, the isomeric propanols, butanols, pentanols, ethers such as diethyl ether, diisopropyl ether, dimethoxyethane, tetrahydro furan, dioxane, nitriles such as acetonitrile or butyronitrile, amides such as dimethylformamide, sulphoxides such as dimethyl sulphoxide, and furthermore sulpholane. Particular preference is given to using alcohols or dimethylformamide.

Suitable bases for the cyclization are all customary acid acceptors.

Preference is given to using tertiary amines such as triethylamine, pyridine, DABCO, DBU, DBN, N,N-dimethylaniline, furthermore alkaline earth metal oxides such as magnesium oxide and calcium oxide, additionally alkali metal carbonates and alkaline earth metal carbonates such as sodium carbonate, potassium carbonate and calcium carbonate, alkali metal hydroxides such as sodium hydroxide and potassium hydroxide, and furthermore alkoxides such as sodium ethoxide or potassium tert-butoxide.

If appropriate, the reaction is carried out in the presence of a phase transfer catalyst. Suitable phase transfer catalysts are for example ammonium compounds such as tetraoctylammonium bromide or benzyltriethylammonium chloride.

The reaction temperature can be varied within a relatively wide range. In general, the reaction is carried out at temperatures between −20° C. and 150° C., preferably between −10° C. and 100° C.

The reaction is generally carried out under atmospheric pressure.

In general, an equimolar amount of base is employed. However, it is also possible to use an excess of base.

Preferred diluents for the subsequent hydrolysis are water/alcohol mixtures such as, for example, water/methanol, water/ethanol or water/propanol or water/amide mixtures such as, for example, water/dimethylformamide (DMF) or water/dimethyl-acetamide.

The hydrolysis is carried out in the presence of a base. Suitable bases include inorganic and organic bases, in particular alkali metal hydroxides such as sodium hydroxide or potassium hydroxide or ammonia.

For the hydrolysis, the reaction temperature can be varied within a relatively wide range. In general, the reaction is carried out at temperatures between −10° C. and 60° C., preferably between 0° C. and 40° C. The reaction is generally carried out under atmospheric pressure.

The cyclization and the removal of the acyl groups can be carried out both as a onepot reaction and in two separate steps.

The compounds of the formula (VI) required as starting materials for the process D) are novel.

The compounds of the formula (VI) are obtained, for example, when compounds of the formula (VII)

(VII)

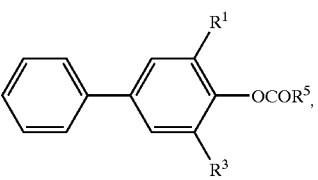

in which

R¹, R³ and R⁵ are each as defined above are reacted with compounds of the formula (VIII)

(VIII)

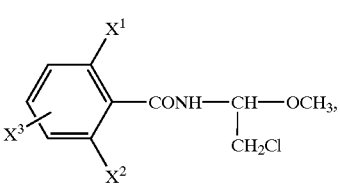

in which

X¹, X² and X³ are each as defined above in the presence of an acid catalyst, for example a Lewis acid such as iron(III) chloride, aluminium chloride or hydrogen fluoride and preferably in the presence of a diluent, for example a halogenated, in particular chlorinated, hydrocarbon such as dichloromethane, at temperatures between −20° C. and 80° C. (cf. the Preparation Examples and also WO 96/18619).

Some of the compounds of the formula (VII) are known (J. Amer Chem. Soc. 61, 1447, 3037 (1939); J. Amer. Chem. Soc. 56, 202 (1934); J. Amer. Chem. Soc. 64, 2219 (1942); J. Amer. Chem. Soc. 89, 2711 (1967); J. Org. Chem. 27, 2671 (1962); J. Indian Chem. Soc. 12, 410 (1935); DE-1 911 520) or can be prepared by known methods, for example by reaction of the corresponding hydroxybiphenyls of the formula (IX) with the acid anhydrides of the formula (X) or the acyl halides (in particular acyl chlorides) of the formula (XI):

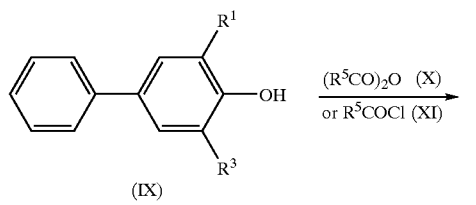

(IX)

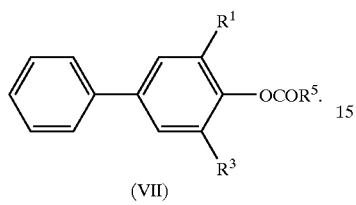

(VII)

Some of the compounds of the formula (IX) are known (see for example J.Org.Chem. 29, 2640 (1964), J. Indian Chem. Soc. 12, 410 (1935), J. Amer. Chem. Soc. 80 3271 (1958), J. Amer. Soc. 56, 202 (1934), J. Org. Chem. 29, 3014 (1964)) or can be prepared by known methods (cf. the Preparation Examples), for example in the following way,

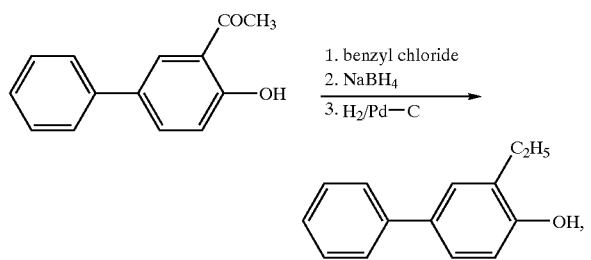

the starting material being known from Bull. Chem. Soc. Jap. 56, 2037 (1983), or according to

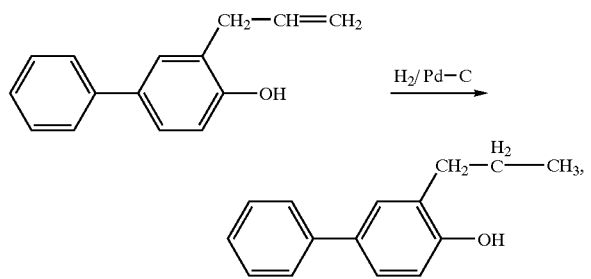

the starting material being known (see J. Amer. Chem. Soc. 80, 3271, (1958)).

The compounds of the formulae (X) and (XI) are generally known and in many cases commercially available or obtainable from the corresponding carboxylic acids in a simple and known manner.

The compounds of the formula (VIII) are known (see for example EP-A-0 594 179, WO 96/18619), or they can be prepared by the methods described therein.

The compounds of the formula (VI) can also be obtained when acyl chlorides of the formula (XII)

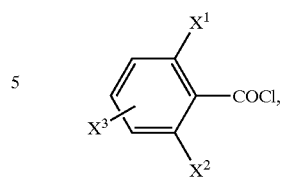

in which
$X^1$, $X^2$ and $X^3$ are each as defined above
are reacted with amino alcohols of the formula (XIII)

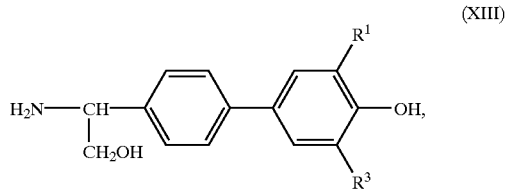

in which
$R^1$ and $R^3$ are each as defined above,
if appropriate in the presence of a diluent (suitable diluents are all solvents which are inert towards these compounds; preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane; the hydrolytic stability of the acyl halide permitting, the reaction can also be carried out in the presence of water) and, if appropriate, in the presence of a base (suitable bases for the reaction are all customary acid acceptors, preference being given to using tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, additionally alkali metal carbonates and alkaline earth metal carbonates, such as sodium carbonate, potassium carbonate and calcium carbonate and alkali metal hydroxides or alkaline earth metal hydroxides such as sodium hydroxide or potassium hydroxide), at temperatures between −20° C. and +100° C., preferably between 0° C. and 30° C., and, if appropriate, the resulting compounds of the formula (XIV)

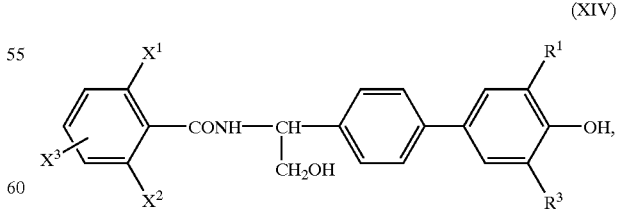

in which
$X^1$, $X^2$, $X^3$, $R^3$ and $R^1$ are each as defined above
are then reacted with a chlorinating agent such as thionyl chloride, phosgene or phosphorus oxychloride, if appropriate in the presence of a diluent, for example hydrocarbons such as toluene, xylene, hexane, cyclohexane, halogenated hydrocarbon such as chlorobenzene, chloroform, methylene chloride or ethers such as diethyl ether, diisopropyl ether, dimethoxyethane, tetrahydrofuran or dioxane, at temperatures between 0° C. and 120° C., preferably between 20° C. and 100° C. (cf. EP-A-0 696 584).

The compounds of the formula (XII) are generally known and in many cases commercially available or obtainable from the corresponding carboxylic acids in a simple and known manner.

The compounds (XIII) are known (cf. EP-A-0 696 584) or can be prepared by methods described therein.

The compounds of the formula (III) furthermore required as starting materials in step A) of the process according to the invention are generally known compounds of organic chemistry. Z represents a customary leaving group, for example halogen (in particular chlorine or bromine), alkylsulphonyloxy (in particular methylsulphonyloxy) or optionally substituted arylsulphonyloxy (in particular phenylsulphonyloxy, p-cholorophenylsulphonyloxy or tolylsulphonyloxy).

Step A) of the process according to the invention is characterized in that a compound of the formula (II) is reacted with a compound of the formula (III), if appropriate in the presence of a diluent and if appropriate in the presence of a base.

Suitable diluents are all customary solvents. Preference is given to using optionally halogenated, aromatic or aliphatic hydrocarbons, ketones, nitrites and amides. Examples include toluene, acetone, acetonitrile, dimethylformamide and dimethylacetamide.

Suitable bases are all customary inorganic and organic bases. Examples include tertiary amines such as triethylamine, DBN, DBU, DABCO, alkali metal hydroxides and alkaline earth metal hydroxides such as, for example, sodium hydroxide, potassium hydroxide and calcium hydroxide, and alkali metal carbonates and alkaline earth metal carbonates such as, for example, sodium carbonate or potassium carbonate.

The reaction temperature can be varied within a relatively wide range. In general, the reaction is carried out at temperatures between −20° C. and 100° C., preferably between 0° C. and 60° C.

The reaction is generally carried out under atmospheric pressure.

The compounds of the formula (II) and the compounds of the formula (III) are generally employed in approximately equimolar amounts. However, it is also possible to employ an excess of the compounds of the formula (III).

Step B) of the process according to the invention is characterized in that compounds of the formula (IV) are subjected to a Claisen rearrangement.

For this purpose, the compounds of the formula (IV) are heated, neat or in the presence of a diluent (chlorobenzene, dichlorobenzene, diethylaniline), to temperatures of from 160° C. to 290° C., preferably 180° C. to 260° C. (see also D. S. Tarbell, The Claisen Rearrangement, Org. Reactions 2, 1 ff (1944)).

Step C) of the process according to the invention is characterized in that compounds of the formula (V) are reacted with compounds of the formula (III), if appropriate in the presence of a diluent and if appropriate in the presence of a base.

For this reaction, which is similar to step A), what has been said for step A) with respect to diluent, base, reaction temperature, etc., also applies.

The active compounds are suitable for controlling animal pests, in particular insects, arachnids and nematodes, encountered in agriculture, in forestry, in the protection of stored products and of materials, and in the hygiene sector, and have good plant safety and low toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, Pediculus humanus corporis,Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example,*Aleurodes brassicae, Bemisia tabaci, Trialeurodes vaporariorum, Aphis gossypii, Brevicoryne brassicae, Cryptomyzus ribis, Aphis fabae, Aphis pormi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,*

Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The compounds of the formula (I) according to the invention in particular have outstanding insecticidal and acaricidal activity.

They are particularly successfully used for controlling plant-damaging insects, for example against mustard beetle larvae (*Phaedon cochleariae*), caterpillars of the owlet moth (*Spodoptera frugiperda*), and green peach aphids (*Myzus persicae*) or for controlling plant-damaging mites, for example against the greenhouse red spider mite (*Tetranychus urticae*).

The active compounds can be converted to the customary formulations, such as solutions, emulsions, wettable powders, suspensions, powders, dusting agents, pastes, soluble powders, granules, suspoemulsion concentrates, natural and synthetic materials impregnated with active compound and very fine capsules in polymeric substances.

These formulations are produced in a known manner, for example by mixing the active compounds with extenders, that is liquid solvents and/or solid carriers, if appropriate with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%, and preferably in addition extenders and/or surfactants.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanatemethyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlophos, pyridaphenthion, pyresmethrin, pyrethrum, pyridaben, pyrimidifen, pyriproxyfen, quinalphos,

RH 5992, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, tetrachlorvinphos, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene and stored-product pests, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Stemostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they have a good development-inhibitory activity against Lucilia cuprina fly larvae.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guineapigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of preferred examples but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec., *Apate monachus, Bostrychus capucins, Heterobostrychus brunneus,* Sinoxylon spec. *Dinoderus minutus.*

Dermapterans, such as *Sirex juvencus, Urocerus gigas, Urocerus gigas taignus* and *Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellant, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30 C., preferably above 45 C.; Substances which are used as such oily and oil-like solvents which have low volatility and are insoluble in water are suitable mineral oils or their aromatic fractions, or mineral-oil-containing solvent mixtures, preferably white spirit, petroleum and/or alkyl-benzene.

Substances which are advantageously used are mineral oils with a boiling range of 170 to 220 C., white spirit with a boiling range of 170 to 220 C., spindle oil with a boiling range of 250 to 350 C., petroleum or aromatics of boiling range of 160 to 280 C., essence of turpentine and the like.

In a preferred embodiment, liquid aliphatic hydrocarbons with a boiling range of 180 to 210 C. or high-boiling mixtures of aromatic and aliphatic hydrocarbons with a boiling range of 180 to 220 C. and/or spindle oil and/or monochloronaphthalene, preferably ∀-monochloronaphthalene, are used.

The organic oily or oil-like solvents of low volatility and having an evaporation number of above 35 and a flashpoint of above 30 C., preferably above 45 C., can be partially replaced by organochemical solvents of high or medium volatility, with the proviso that the solvent mixture also has an evaporation number of above 35 and a flashpoint of above 30 C., preferably above 45 C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of; or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binder. In addition, colorants, pigments, water repellants, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, diclofluanid, tolylfluanid, 3-iodo-2propinyl-butyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLE

Example (I-1)

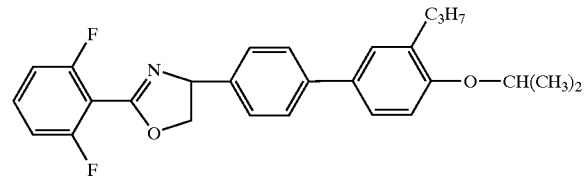

2-(2,6-Difluorophenyl)-4-(4-(4-propyl-2-oxy)-3-n-propylphenyl)phenyl-2-oxazoline: 1.5 g (3.8 mmol) of 2-(2,6-difluorophenyl)-4-(4-(4-hydroxy-3-n-propylphenyl) phenyl)-2-oxazoline in 30 ml of acetonitrile with 0.6 g (4.5 mmol) of potassium carbonate and 6.0 g (48 mmol) of 2-bromopropane are heated under reflux for 10 hours. The mixture is then poured into water and the product is extracted with ethyl acetate. The organic phase is dried and concentrated under reduced pressure and the residue is purified over silica gel using the system cyclohexane/ethyl acetate (2:1).

Yield: 0.45 g; Mp. 60–62° C.

Example (I-342)

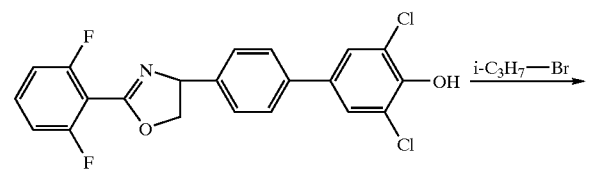

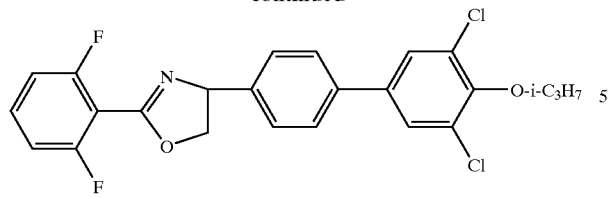

2-(2,6-Difluorophenyl)-4-(4-(4-(propyl-2-oxy)-3,5-dichlorophenyl)phenyl)-4,5-dihydro-oxazoline 2.9 g (7 mmol) of 2-(2,6-difluorophenyl)-4-(4-(4-hydroxy-3,5-dichlorophenyl)phenyl)-4,5-dihydro-oxazoline in 50 ml of acetonitrile and 1.9 g (14 mmol) of potash and 8.6 g (70 mmol) of 2-propyl bromide are heated under reflux for 6 hours. The reaction mixture is poured into water and the product is extracted with methylene chloride. After washing with water, the organic phase is evaporated under reduced pressure and the residue is chromatographed over silica gel using the system cyclohexane/ethyl acetate (2:1). 1.6 g of 2-(2,6-difluorophenyl)-4-(4-(4-(propyl-2-oxy)-3,5-dichlorophenyl)phenyl)-4,5-dihydro-oxazoline are obtained as an oil of log p (pH 7.5)=5.65. (Yield: 49.5% of theory).

Similarly, and/or according to the general preparation procedures, the compounds of the formula (I) listed in the tables that follow are obtained:

TABLE 1

(I)

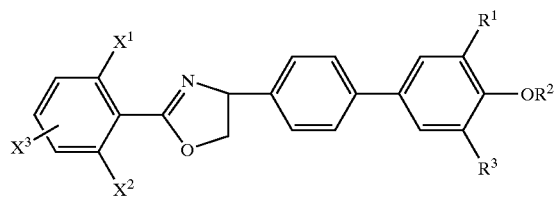

| Ex. No. | $X^1$ | $X^2$ | $X^3$ | $R^1$ | $R^2$ | $R^3$ | physical characterization |
|---|---|---|---|---|---|---|---|
| I-2 | F | F | H | —CH$_2$—CH$_2$—CH$_3$ | —CH(CH$_3$)$_2$ | H | Mp. 60–62° C. |
| I-3 | F | F | H | CH$_3$ | —CH(CH$_3$)$_2$ | H | Mp. 68–70° C. |
| I-4 | F | F | H | CH$_3$ | —CH$_2$—C$_6$H$_4$—Cl | H | Mp. 126–130° C. |
| I-5 | F | F | H | —CH$_2$—CH$_2$—CH$_3$ | —CH$_2$—C$_6$H$_4$—CF$_3$ | H | Mp. 106–108° C. |
| I-6 | F | F | H | CH$_3$ | —CH$_2$—C$_6$H$_4$—CF$_3$ | H | Mp. 119–122° C. |
| I-7 | F | F | H | CH$_3$ | —CH(CH$_3$)C$_2$H$_5$ | H | log p*: 5.60 (pH = 7.5) |
| I-8 | H | CH$_3$ | H | —CH$_2$—CH$_2$—CH$_3$ | —CH$_2$—C$_6$H$_4$—CF$_3$ | H | log p: 7.07 (pH = 7.5) |
| I-9 | H | CH$_3$ | H | —CH$_2$—CH$_2$—CH$_3$ | —CH(CH$_3$)C$_2$H$_5$ | H | log p: 7.28 (pH = 7.5) |
| I-10 | F | F | H | —CH$_2$—CH$_2$—CH$_3$ | —CH(CH$_3$)C$_2$H$_5$ | H | log p: 6.33 (pH = 7.5) |
| I-11 | F | F | H | —CH$_2$CH$_2$—CH$_3$ | —CH$_2$—C$_6$H$_4$—Cl | H | Mp. 106–108° C. |
| I-12 | H | Cl | H | CH$_3$ | —CH(CH$_3$)$_2$ | H | log p: 5.56 (pH = 7.5) |
| I-13 | H | Cl | H | CH$_3$ | —CH$_2$—C$_6$H$_4$—Cl | H | log p: 6.15 (pH = 7.5) |
| I-14 | H | Br | H | CH$_3$ | —CH(CH$_3$)$_2$ | H | log p: 5.63 (pH = 7.5) |

TABLE 1-continued (I)

| Ex. No. | X¹ | X² | X³ | R¹ | R² | R³ | physical characterization |
|---|---|---|---|---|---|---|---|
| I-15 | H | Br | H | $CH_3$ | $-CH_2-C_6H_4-CF_3$ (4-CF₃) | H | Mp. 88–93° C. |
| I-16 | H | Br | H | $CH_3$ | $-CH(CH_3)C_2H_5$ | H | log p: 6.12 (pH = 7.5) |
| I-17 | H | Cl | H | $CH_3$ | $-CH(CH_3)-CH(OH)CH_3$ | H | log p: 4.08/4.13 (pH = 7.5) |
| I-18 | H | Br | H | $CH_3$ | $-CH_2-C_6H_4-NO_2$ (3-NO₂) | H | Mp. 118–120° C. |
| I-19 | F | F | H | Cl | $-CH(CH_3)_2$ | H | log p (pH 7.5): 4.96 |
| I-20 | F | F | H | Cl | $-CH_2-C_6H_4-Cl$ (4-Cl) | H | Mp. 125–128° C. |
| I-21 | F | F | H | Cl | $-CH_2-C_6H_5$ | H | Mp. 126° C. |
| I-22 | F | F | H | Cl | $-CH_2-C_6H_4-C(CH_3)_3$ (4-tBu) | H | Mp. 148° C. |
| I-23 | F | F | H | Cl | $-CH_2-C_6H_4-NO_2$ (4-NO₂) | H | Mp. 122° C. |
| I-24 | F | F | H | Cl | $-CH_2-CH(CH_3)_2$ | H | Mp. 78–80° C. |
| I-25 | F | F | H | Cl | $-(CH_2)_3CH_3$ | H | Mp. 94–96° C. |
| I-26 | F | F | H | Cl | $-CH_2-CH=CH_2$ | H | Mp. 85° C. |
| I-27 | F | F | H | Cl | $-CH_2-C(CH_3)=CH_2$ | H | Mp. 83–85° C. |
| I-28 | F | F | H | Cl | $-CH_2CH_3$ | H | Mp. 130–132° C. |
| I-29 | F | F | H | Cl | $-CH_2-$(tetrahydronaphthyl) | H | Isomer mixture log p 6.24 and 6.32 (pH = 7.5) |
| I-30 | H | Cl | H | Cl | $-CH(CH_3)_2$ | H | log p (pH 7.5): 5.37 |
| I-31 | F | F | H | Cl | $-CH_2-$cyclopropyl | H | Mp. 84–85° C. |
| I-32 | H | F | H | Cl | $CH(CH_3)_2$ | H | log p (pH 7.5): 5.04 |
| I-33 | H | Cl | H | Cl | $-CH_2-C_6H_4-CF_3$ (4-CF₃) | H | Mp. 158–160° C. |
| I-34 | H | Cl | H | Cl | $CH_2CH(CH_3)_2$ | H | log p (pH 7.5): 6.03 |
| I-35 | H | Cl | H | $CH_2-CH_2-CH_3$ | $CH(CH_3)CH(OH)CH_3$ | H | log p: 4.79/4.86 (pH 7.5) |
| I-36 | H | Cl | H | $CH_2-CH_2-CH_3$ | $CH(CH_3)_2$ | H | log p: 6.35 (pH 7.5) |

TABLE 1-continued

(I)

| Ex. No. | X¹ | X² | X³ | R¹ | R² | R³ | physical characterization |
|---|---|---|---|---|---|---|---|
| I-37 | H | Cl | H | CH$_2$—CH$_2$—CH$_3$ | CH$_2$CH(CH$_3$)$_2$ | H | log p: 6.95 (pH 7.5) |
| I-38 | H | Cl | H | CH$_2$—CH$_2$—CH$_3$ | —CH$_2$—C$_6$H$_4$—Cl | H | log p: 6.79 (pH 7.5) |
| I-39 | H | Cl | H | CH$_2$—CH$_2$—CH$_3$ | CH$_2$—CH(OH)CH$_3$ | H | log p: 4.47 (pH 7.5) |
| I-40 | H | Br | H | CH$_2$—CH$_2$—CH$_3$ | CH(CH$_3$)$_2$ | H | log p: 6.40 (pH 7.5) |
| I-41 | H | I | H | CH$_3$ | —CH$_2$—C$_6$H$_4$—Cl | H | Mp. 88–92° C. |
| I-42 | H | Br | H | CH$_2$—CH$_2$—CH$_3$ | CH$_2$C≡CH | H | Mp. 82–84° C. |
| I-43 | H | Br | H | CH$_2$—CH$_2$—CH$_3$ | —CH$_2$—C$_6$H$_4$—Cl | H | log p: 6.84 (pH 7.5) |
| I-44 | F | F | H | CH$_3$ | CH(CH$_3$)$_2$ | CH$_3$ | log p: 5.23 (pH 7.5) |
| I-45 | F | F | H | CH$_2$CH=CH$_2$ | CH(CH$_3$)$_2$ | H | Mp. 86–87° C. |
| I-46 | F | F | H | CH$_2$CH=CH$_2$ | —CH$_2$—C$_6$H$_4$—Cl | H | Mp. 96–98° C. |
| I-47 | F | F | H | CH$_3$ | CH$_2$C(CH$_3$)=CH$_2$ | H | Mp. 106–108° C. |
| I-48 | F | F | H | CH$_3$ | CH$_2$—CH$_2$—CH$_3$ | H | Mp. 112–114° C. |
| I-49 | F | F | H | CH$_3$ | —CH$_2$—C$_6$H$_3$(Cl)$_2$ (2,4-diCl) | H | Mp. 118–120° C. |
| I-50 | H | Br | H | CH$_2$—CH$_2$—CH$_3$ | —CH$_2$—C$_6$H$_3$(Cl)$_2$ (3,4-diCl) | H | Mp. 108–110° C. |
| I-51 | H | Br | H | CH$_2$—CH$_2$—CH$_3$ | —CH$_2$—C$_6$H$_4$—CF$_3$ | H | Mp. 117–119° C. |
| I-52 | H | CH$_3$ | H | CH$_2$—CH$_2$—CH$_3$ | CH(CH$_3$)$_2$ | H | log p: 6.78 (pH 7.5) |
| I-53 | F | F | H | CH$_2$—CH$_2$—CH$_3$ | —CH$_2$—C$_6$H$_4$—OCF$_3$ | H | Mp. 78–80° C. |
| I-54 | F | F | H | CH$_2$CH=CH$_2$ | CH$_2$CH=CH$_2$ | H | Mp. 106–108° C. |
| I-55 | H | CH$_3$ | H | CH$_3$ | CH$_2$CH=CH$_2$ | H | log p: 5.64 (pH 7.5) |

TABLE 1-continued

(I)

| Ex. No. | X$^1$ | X$^2$ | X$^3$ | R$^1$ | R$^2$ | R$^3$ | physical characterization |
|---|---|---|---|---|---|---|---|
| I-56 | H | CH$_3$ | H | CH$_3$ | 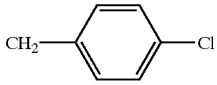 | H | log p: 6.50 (pH 7.5) |
| I-57 | H | I | H | CH$_2$—CH$_2$—CH$_3$ | CH(CH$_3$)$_2$ | H | log p: 6.59 (pH 7.5) |
| I-58 | H | I | H | CH$_2$—CH$_2$—CH$_3$ | 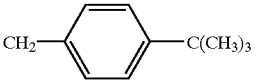 | H | log p: 7.03 (pH 7.5) |
| I-59 | F | F | H | CH$_2$CH=CH$_2$ | CH(CH$_3$)C$_2$H$_5$ | H | log p: 5.95 (pH 7.5) |
| I-60 | F | F | H | CH$_2$—CH$_2$—CH$_3$ | 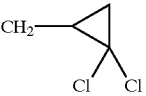 | H | log p: 7.14 (pH 7.5) |
| I-61 | H | Br | H | CH$_3$ | 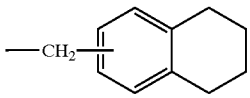 | H | log p: 5.76 (pH 7.5) |
| I-62 | H | I | H | CH$_2$—CH$_2$—CH$_3$ | CH$_2$CH=CH$_2$ | H | Mp. 73–75° |
| I-63 | F | F | H | C$_2$H$_5$ | CH(CH$_3$)$_2$ | H | log p: 5.54 (pH 7.5) |
| I-64 | H | CH$_3$ | H | CH$_2$—CH$_2$—CH$_3$ | CH$_2$CH(CH$_3$)$_2$ | H | log p: 4.48 (pH 7.5) |
| I-65 | F | F | H | CH$_3$ |  | H | log p: 6.44/6.55 (pH 7.5) |
| I-66 | F | F | H | CH$_2$—CH$_2$—CH$_3$ | CH$_2$—CH$_2$—CH$_3$ | H | Mp. 90–92° C. |
| I-67 | H | I | H | CH$_3$ | CH(CH$_3$)$_2$ | H | log p: 5.81 (pH 7.5) |
| I-68 | F | F | H | C$_2$H$_5$ | 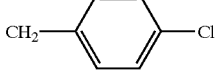 | H | Mp. 118–120° C. |
| I-69 | H | Br | H | CH$_3$ | CH(CH$_3$)CH(OH)CH$_3$ | H | log p: 4.15/4.20 (pH 7.5) |
| I-70 | H | CH$_3$ | H | CH$_3$ | CH(CH$_3$)$_2$ | H | log p: 6.02 (pH 7.5) |
| I-71 | Cl | F | H | Cl | CH(CH$_3$)$_2$ | H | log p: 5.25 (pH 7.5) |
| I-72 | Cl | F | H | Cl |  | H | Mp. 136° C. |
| I-73 | Cl | F | H | Cl | CH$_2$C≡CH | H | Mp. 138° C. |
| I-74 | Cl | F | H | Cl |  | H | Mp. 126° C. |
| I-75 | Cl | F | H | Cl | CH$_2$—CH$_2$—CH$_3$ | H | Mp. 120° C. |
| I-76 | Cl | F | H | Cl | CH(CH$_3$)C$_2$H$_5$ | H | log p: 5.69 (pH 7.5) |
| I-77 | Cl | F | H | Cl | CH$_2$CH(CH$_3$)$_2$ | H | log p: 5.89 (pH 7.5) |

TABLE 1-continued

(I)

| Ex. No. | X¹ | X² | X³ | R¹ | R² | R³ | physical characterization |
|---|---|---|---|---|---|---|---|
| I-78 | Cl | F | H | Cl | 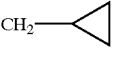 | H | log p: 5.94 (pH 7.5) |
| I-79 | Cl | F | H | Cl | 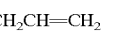 | H | Mp. 116° C. |
| I-80 | Cl | F | H | Cl | $CH_2CH=CH_2$ | H | log p: 4.99 (pH 7.5) |
| I-81 | Cl | F | H | Cl | 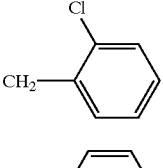 | H | log p: 5.94 (pH 7.5) |
| I-82 | Cl | F | H | $CH_2-CH_2-CH_3$ | 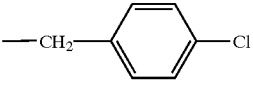 | H | Mp. 92° C. |
| I-83 | Cl | F | H | Cl | $n\text{-}C_6H_{13}$ | H | log p: 6.68 (pH 7.5) |
| I-84 | Cl | F | H | $CH_2-CH_2-CH_3$ | $CH_2-CH_2-CH_3$ | H | Mp. 80° C. |
| I-85 | Cl | F | H | $CH_2-CH_2-CH_3$ | $CH(CH_3)_2$ | H | log p: 6.20 (pH 7.5) |
| I-86 | Cl | F | H | $CH_2-CH_2-CH_3$ | $CH(CH_3)C_2H_5$ | H | log p: 6.62 (pH 7.5) |
| I-87 | H | F | H | Cl | $CH_2-CH_2-CH_3$ | H | log p: 5.22 (pH 7.5) |
| I-88 | H | F | H | Cl | 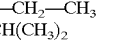 | H | Mp. 120° C. |
| I-89 | H | F | H | Cl | $CH(CH_3)C_2H_5$ | H | log p: 5.49 (pH 7.5) |
| I-90 | H | F | H | Cl | $CH_2CH(CH_3)_2$ | H | log p: 5.70 (pH 7.5) |
| I-91 | Cl | F | H | $CH_2-CH_2-CH_3$ | $CH_2C{\equiv}CH$ | H | Mp. 82° C. |
| I-92 | Cl | F | H | $CH_2-CH_2-CH_3$ | 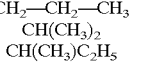 | H | log p: 6.78 (pH 7.5) |
| I-93 | Cl | F | H | Cl | 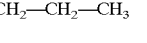 | H | Mp. 140° C. |
| I-94 | Cl | F | H | $CH_2-CH_2-CH_3$ |  | H | Mp. 128° C. |
| I-95 | H | F | H | Cl | 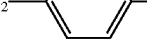 | H | Mp. 154° C. |

TABLE 1-continued

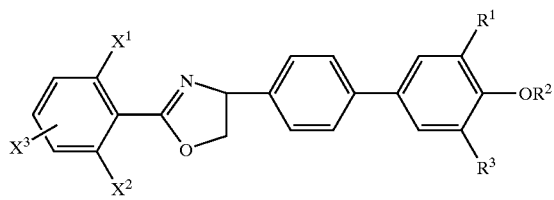

(I)

| Ex. No. | X¹ | X² | X³ | R¹ | R² | R³ | physical characterization |
|---|---|---|---|---|---|---|---|
| I-96 | H | F | H | Cl | n-$C_6H_{13}$ | H | log p: 6.48 (pH 7.5) |
| I-97 | H | F | H | Cl | $CH_2CH=CH_2$ | H | Mp. 92° C. |
| I-98 | H | F | H | Cl | $CH_2$-C₆H₄-$OCF_3$ | H | Mp. 138° C. |
| I-99 | Cl | F | H | Cl | —$CH_2$-C₆H₄-$CF_3$ | H | Mp. 144° C. |
| I-100 | Cl | F | H | $CH_2$—$CH_2$—$CH_3$ | —$CH_2$-C₆H₄-$CF_3$ | H | Mp. 148° C. |
| I-101 | Cl | F | H | $CH_2$—$CH_2$—$CH_3$ | $CH_2$-C₆H₄-$OCF_3$ | H | Mp. 130° C. |
| I-102 | Cl | F | H | $CH_2$—$CH_2$—$CH_3$ | $CH_2$-C₆H₄-$SCF_3$ | H | Mp. 94° C. |
| I-103 | Cl | F | H | $CH_2$—$CH_2$—$CH_3$ | n-$C_6H_{13}$ | H | Mp. 62° C. |
| I-104 | Cl | F | H | $CH_2$—$CH_2$—$CH_3$ | $CH_2CH(CH_3)_2$ | H | log p: 6.82 (pH 7.5) |
| I-105 | Cl | F | H | $CH_2$—$CH_2$—$CH_3$ | $CH_2CH=CH_2$ | H | Mp. 48° C. |
| I-106 | Cl | F | H | $CH_3$ | $CH_2$-C₆H₄-Cl (4-Cl) | H | Mp. 131° C. |
| I-107 | Cl | F | H | $CH_3$ | $CH_2$-C₆H₄-Cl (2-Cl) | H | Mp. 120° C. |
| I-108 | H | F | H | $CH_3$ | —$CH_2$-C₆H₄-Cl (4-Cl) | H | Mp. 96° C. |
| I-109 | H | F | H | $CH_3$ | $CH_2$-C₆H₃-(Cl)₂ (3,4-diCl) | H | log p: 6.25 (pH 7.5) |

TABLE 2

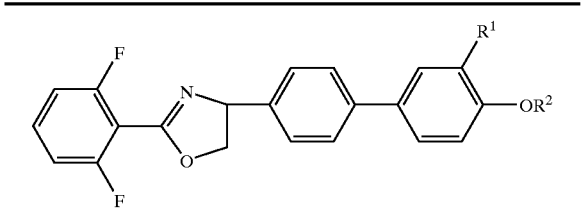

| Ex. No. | R¹ | R² | physical characterization |
|---|---|---|---|
| I-110 | $CH_3$ | $n\text{-}C_6H_{13}$ | Mp. 95–97° C. |
| I-111 | $CH_3$ | $CH_2CH=CH_2$ | Mp. 82–84° C. |
| I-112 | $CH_3$ | $CH_2C\equiv CH$ | Mp. 116–18° C. |
| I-113 | $CH_3$ | $CH_2$-(3,4-dichlorophenyl) | Mp. 109–11° C. |
| I-114 | $CH_3$ | $CH_2CH_2$-(4-chlorophenyl) | log p: 5.90 (pH 7.5) |
| I-115 | $n\text{-}C_3H_7$ | $CH_2CH=CH_2$ | |
| I-116 | $n\text{-}C_3H_7$ | $CH_2C\equiv CH$ | Mp. 119–21° C. |
| I-117 | $n\text{-}C_3H_7$ | $CH_2$-cyclopropyl | |
| I-118 | $n\text{-}C_3H_7$ | cyclohexyl | |
| I-119 | $n\text{-}C_3H_7$ | $CH_2$-(3,4-dichlorophenyl) | Mp. 95–96° C. |
| I-120 | $n\text{-}C_3H_7$ | $CH_2$-(4-$OCF_3$-phenyl) | Mp. 78–80° C. |
| I-121 | $n\text{-}C_3H_7$ | $CH_2$-(3,4-dichlorophenyl) | |
| I-122 | $n\text{-}C_3H_7$ | $CH_2CH_2$-(4-chlorophenyl) | Mp. 72–74° C. |
| I-123 | $CH_2CH=CH_2$ | $CH_2C\equiv CH$ | Mp. 82–85° C. |
| I-124 | $CH_2CH=CH_2$ | $CH_2$-(2-chlorophenyl) | |

TABLE 2-continued

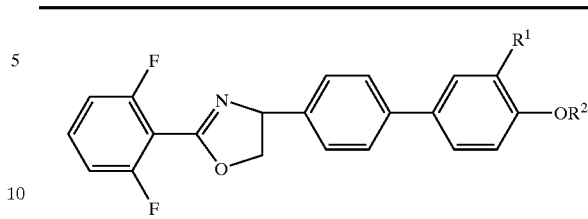

| Ex. No. | R¹ | R² | physical characterization |
|---|---|---|---|
| I-125 | $CH_2CH=CH_2$ | $CH_2$-(3,4-dichlorophenyl) | Mp. 106–108° C. |
| I-126 | $CH_2CH=CH_2$ | $CH_2$-(4-$CF_3$-phenyl) | Mp. 75–77° C. |
| I-127 | $CH_2CH=CH_2$ | $CH_2$-(4-$OCF_3$-phenyl) | Mp. 76–78° C. |
| I-128 | $CH_2CH=CH_2$ | $CH_2$-(4-$SCF_3$-phenyl) | Mp. 75–77° C. |
| I-129 | $CH_2CH=CH_2$ | $CH_2$-(2,4-dichlorophenyl) | log p: 6.73 (pH 7.5) |
| I-130 | $CH_2CH=CH_2$ | $CH_2CH_2$-(4-chlorophenyl) | Mp. 83–85° C. |

TABLE 3

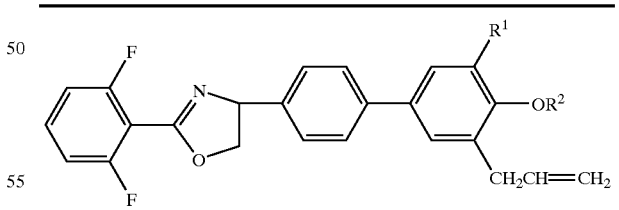

| Ex. No. | R¹ | R² | physical characterization |
|---|---|---|---|
| I-131 | $CH_3$ | $i\text{-}C_3H_7$ | |
| I-132 | $CH_3$ | $s\text{-}C_4H_9$ | |
| I-133 | $CH_3$ | $CH_2CH=CH_2$ | |
| I-134 | $CH_3$ | $CH_2$-(4-chlorophenyl) | Mp. 75° C. |

TABLE 3-continued

Structure: 2-(2,6-difluorophenyl)-oxazoline linked to biphenyl with R¹, OR², and CH₂CH=CH₂ substituents

| Ex. No. | R¹ | R² | physical characterization |
|---|---|---|---|
| I-135 | CH₃ | CH₂-(2,3-dichlorophenyl) | |
| I-136 | CH₃ | CH₂-(4-CF₃-phenyl) | Mp. 76° C. |
| I-137 | CH₃ | CH₂CH₂-(4-Cl-phenyl) | |
| I-138 | CH₂CH=CH₂ | i-C₃H₇ | Mp. 78–80° C. |
| I-139 | CH₂CH=CH₂ | s-C₄H₉ | log p: 6.39 (pH 7.5) |
| I-140 | CH₂CH=CH₂ | CH₂CH=CH₂ | Mp. 75–77° C. |
| I-141 | CH₂CH=CH₂ | CH₂-(4-Cl-phenyl) | Mp. 75–76° C. |
| I-142 | CH₂CH=CH₂ | CH₂-(3,4-dichlorophenyl) | log p: 6.99 (pH 7.5) |
| I-143 | CH₂CH=CH₂ | CH₂-(4-CF₃-phenyl) | Mp. 73–75° C. |
| I-144 | CH₂CH=CH₂ | CH₂CH₂-(4-Cl-phenyl) | |

TABLE 4

Structure: 2-(2-methylphenyl)-oxazoline linked to biphenyl with R¹, OR², and CH₂CH=CH₂ substituents

| Ex. No. | R¹ | R² | physical characterization |
|---|---|---|---|
| I-145 | Cl | n-C₆H₁₃ | |
| I-146 | Cl | i-C₃H₇ | log p: 6.75 (pH 7.5) |
| I-147 | Cl | CH₂C≡CH | |
| I-148 | Cl | CH₂-(4-Cl-phenyl) | log p: 7.32 (pH 7.5) |
| I-149 | Cl | CH₂-(3,4-dichlorophenyl) | log p: 7.36 (pH 7.5) |
| I-150 | Cl | CH₂-(4-CF₃-phenyl) | log p: 7.16 (pH 7.5) |

TABLE 5

Structure: 2-(2-methylphenyl)-oxazoline linked to biphenyl with R¹ and OR² substituents (no allyl group)

| Ex. No. | R¹ | R² | physical characterization |
|---|---|---|---|
| I-151 | CH₃ | CH₂C≡CH | |
| I-152 | CH₃ | CH₂-(4-Cl-phenyl) | log p: 6.51 (pH 7.5) |
| I-153 | CH₃ | CH₂CH₂-(4-Cl-phenyl) | |
| I-154 | Cl | i-C₃H₇ | Mp. 108–10° C. |
| I-155 | Cl | CH₂CH=CH₂ | log p: 5.47 (pH 7.5) |
| I-156 | Cl | CH₂C≡CH | log p: 4.81 (pH 7.5) |
| I-157 | Cl | CH₂-(4-Cl-phenyl) | Mp. 125–27° C. |
| I-158 | Cl | CH₂-(3,4-dichlorophenyl) | Mp. 110–12° C. |
| I-159 | Cl | CH₂-(4-CF₃-phenyl) | Mp. 125–28° C. |

TABLE 5-continued

Structure: 2-(2-methylphenyl)-4,5-dihydrooxazole with biphenyl-OR² and R¹ substituent

| Ex. No. | R¹ | R² | physical characterization |
|---|---|---|---|
| I-160 | Cl | CH₂-C₆H₄-OCF₃ (para) | Mp. 97–99° C. |
| I-161 | Cl | CH₂CH₂-C₆H₄-Cl (para) | |

TABLE 6

Structure: 2-(2-fluoro-6-chlorophenyl)-4,5-dihydrooxazole with biphenyl-OR² and R¹ substituent

| Ex. No. | R¹ | R² | physical characterization |
|---|---|---|---|
| I-162 | CH₃ | n-C₃H₇ | Mp. 98° C. |
| I-163 | CH₃ | i-C₃H₇ | log p: 5.45 (pH 7.5) |
| I-164 | CH₃ | i-C₄H₉ | Mp. 91° C. |
| I-165 | CH₃ | s-C₄H₉ | log p: 5.93 (pH 7.5) |
| I-166 | CH₃ | n-C₆H₁₃ | Mp. 68° C. |
| I-167 | CH₃ | CH₂CH=CH₂ | Mp. 77° C. |
| I-168 | CH₃ | CH₂C≡CH | Mp. 149° C. |
| I-169 | CH₃ | CH₂-C₆H₃-3,4-Cl₂ | Mp. 148° C. |
| I-170 | CH₃ | CH₂-C₆H₄-CF₃ (para) | Mp. 148° C. |
| I-171 | CH₃ | CH₂-C₆H₄-OCF₃ (para) | Mp. 113° C. |
| I-172 | CH₃ | CH₂-C₆H₄-SCF₃ (para) | log p: 6.37 (pH 7.5) |
| I-173 | CH₃ | CH₂CH₂-C₆H₄-Cl (para) | log p: 6.21 (pH 7.5) |
| I-174 | n-C₃H₇ | CH₂CH₂-C₆H₄-Cl (para) | log p: 6.82 (pH 7.5) |
| I-175 | Cl | CH₂CH₂-C₆H₄-Cl (para) | |
| I-176 | CH₂CH=CH₂ | n-C₃H₇ | log p: 5.98 (pH 7.5) |
| I-177 | CH₂CH=CH₂ | i-C₃H₇ | log p: 5.82 (pH 7.5) |
| I-178 | CH₂CH=CH₂ | i-C₄H₉ | log p: 6.47 (pH 7.5) |
| I-179 | CH₂CH=CH₂ | s-C₄H₉ | log p: 6.33 (pH 7.5) |
| I-180 | CH₂CH=CH₂ | n-C₆H₁₃ | Mp. 48° C. |
| I-181 | CH₂CH=CH₂ | CH₂CH=CH₂ | log p: 5.49 (pH 7.5) |
| I-182 | CH₂CH=CH₂ | CH₂C≡CH | log p: 4.81 (pH 7.5) |
| I-183 | CH₂CH=CH₂ | CH₂-C₆H₄-Cl (para) | log p: 6.30 (pH 7.5) |
| I-184 | CH₂CH=CH₂ | CH₂-C₆H₃-3,4-Cl₂ | log p: 6.73 (pH 7.5) |
| I-185 | CH₂CH=CH₂ | CH₂-C₆H₄-CF₃ (para) | Mp. 73° C. |
| I-186 | CH₂CH=CH₂ | CH₂-C₆H₄-OCF₃ (para) | log p: 6.27 (pH 7.5) |
| I-187 | CH₂CH=CH₂ | CH₂-C₆H₄-SCF₃ (para) | log p: 6.56 (pH 7.5) |
| I-188 | CH₂CH=CH₂ | CH₂CH₂-C₆H₄-Cl (para) | log p: 6.45 (pH 7.5) |

TABLE 7

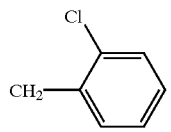

| Ex. No. | R¹ | R² | physical characterization |
|---|---|---|---|
| I-189 | CH₃ | n-C₃H₇ | Mp. 79° C. |
| I-190 | CH₃ | i-C₃H₇ | log p: 5.23 (pH 7.5) |
| I-191 | CH₃ | i-C₄H₉ | log p: 5.89 (pH 7.5) |
| I-192 | CH₃ | s-C₄H₉ | log p: 5.70 (pH 7.5) |
| I-193 | CH₃ | n-C₆H₁₃ | Mp 68° C. |
| I-194 | CH₃ | CH₂CH=CH₂ | Mp. 71° C. |
| I-195 | CH₃ | CH₂C≡CH | Mp. 99° C. |
| I-196 | CH₃ | CH(CH₃)C≡CH | log p: 4.68 (pH 7.5) |
| I-197 | CH₃ | 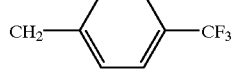 | log p: 5.91 (pH 7.5) |
| I-198 | CH₃ | 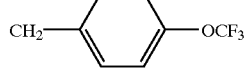 | Mp. 109° C. |
| I-199 | CH₃ | 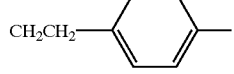 | log p: 5.90 (pH 7.5) |
| I-200 | CH₃ |  | log p: 5.98 (pH 7.5) |
| I-201 | n-C₃H₇ | n-C₃H₇ | Mp. 73° C. |
| I-202 | n-C₃H₇ | i-C₃H₇ | log p: 6.03 (pH 7.5) |
| I-203 | n-C₃H₇ | n-C₄H₉ | Mp. 79° C. |
| I-204 | n-C₃H₇ | i-C₄H₉ | log p: 6.61 (pH 7.5) |
| I-205 | n-C₃H₇ | s-C₄H₉ | log p: 6.47 |
| I-206 | n-C₃H₇ | n-C₆H₁₃ | Mp. 74° C. |
| I-207 | n-C₃H₇ | CH₂CH=CH₂ | Mp. 72° C. |
| I-208 | n-C₃H₇ | CH₂C≡CH | Mp. 100° C. |
| I-209 | n-C₃H₇ | CH(CH₃)C≡CH | log p: 5.32 (pH 7.5) |
| I-210 | n-C₃H₇ | 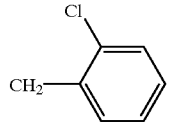 | log p: 6.45 (pH 7.5) |
| I-211 | n-C₃H₇ | 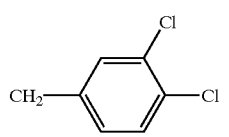 | log p: 6.56 (pH 7.5) |
| I-212 | n-C₃H₇ | 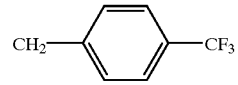 | log p: 6.93 (pH 7.5) |

TABLE 7-continued

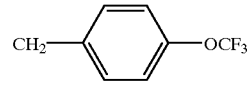

| Ex. No. | R¹ | R² | physical characterization |
|---|---|---|---|
| I-213 | n-C₃H₇ | 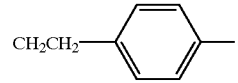 | log p: 6.35 (pH 7.5) |
| I-214 | n-C₃H₇ | 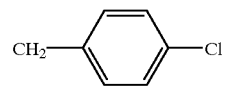 | log p: 6.44 (pH 7.5) |
| I-215 | n-C₃H₇ | 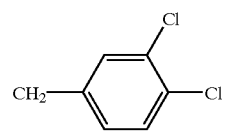 | log p: 6.57 (pH 7.5) |
| I-216 | Cl | n-C₃H₇ | log p: 5.22 (pH 7.5) |
| I-217 | Cl | i-C₄H₉ | log p: 5.70 (pH 7.5) |
| I-218 | Cl | s-C₄H₉ | log p: 5.49 (pH 7.5) |
| I-219 | Cl | n-C₆H₁₃ | log p: 6.48 (pH 7.5) |
| I-220 | Cl | CH₂CH=CH₂ | Mp. 92° C. |
| I-221 | Cl | CH₂C≡CH | log p: 4.16 (pH 7.5) |
| I-222 | Cl | CH(CH₃)C≡CH | log p: 4.58 (pH 7.5) |
| I-223 | Cl | 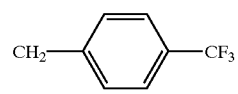 | Mp. 120° C. |
| I-224 | Cl | 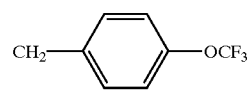 | Mp. 154° C. |
| I-225 | Cl | 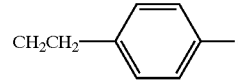 | Mp. 140° C. |
| I-226 | Cl |  | Mp. 138° C. |
| I-227 | Cl |  | log p: 5.91 (pH 7.5) |

TABLE 8

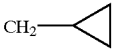

| Ex. No. | R¹ | R² | physical characterization |
|---|---|---|---|
| I-228 | CH₃ | n-C₃H₇ | |
| I-229 | CH₃ | i-C₃H₇ | log p: 5.56 (pH 7.5) |
| I-230 | CH₃ | i-C₄H₉ | |
| I-231 | CH₃ | n-C₆H₁₃ | Mp. 68–70° C. |
| I-232 | CH₃ | CH₂CH=CH₂ | Mp. 85–87° C. |
| I-233 | CH₃ | CH₂C≡CH | Mp. 96–98° C. |
| I-234 | CH₃ | CH₂-cyclopropyl | log p: 5.57 (pH 7.5) |
| I-235 | CH₃ | CH₂-(3,4-dichlorophenyl) | log p: 6.56 (pH 7.5) |
| I-236 | CH₃ | CH₂-(4-CF₃-phenyl) | log p: 6.06 (pH 7.5) |
| I-237 | CH₃ | CH₂-(4-OCF₃-phenyl) | Mp. 83–84° C. |
| I-238 | CH₃ | CH₂CH₂-(4-Cl-phenyl) | log p: 6.31 (pH 7.5) |
| I-239 | n-C₃H₇ | n-C₃H₇ | |
| I-240 | n-C₃H₇ | i-C₃H₇ | log p: 6.35 (pH 7.5) |
| I-241 | n-C₃H₇ | n-C₆H₁₃ | |
| I-242 | n-C₃H₇ | CH₂CH=CH₂ | |
| I-243 | n-C₃H₇ | CH₂C≡CH | |
| I-244 | n-C₃H₇ | CH₂-cyclopropyl | |
| I-245 | n-C₃H₇ | CH₂-(3,4-dichlorophenyl) | |
| I-246 | n-C₃H₇ | CH₂-(4-CF₃-phenyl) | |
| I-247 | n-C₃H₇ | CH₂-(4-OCF₃-phenyl) | |
| I-248 | n-C₃H₇ | CH₂CH₂-(4-Cl-phenyl) | |

TABLE 8-continued

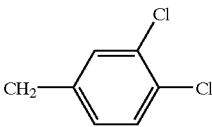

| Ex. No. | R¹ | R² | physical characterization |
|---|---|---|---|
| I-249 | CH₂CH=CH₂ | n-C₃H₇ | Mp. 56–58° C. |
| I-250 | CH₂CH=CH₂ | i-C₃H₇ | log p: 5.93 (pH 7.5) |
| I-251 | CH₂CH=CH₂ | i-C₄H₉ | log p: 6.52 (pH 7.5) |
| I-252 | CH₂CH=CH₂ | CH₂CH=CH₂ | Mp. 58–60° C. |
| I-253 | CH₂CH=CH₂ | CH₂C≡CH | Mp. 74–76° C. |
| I-254 | CH₂CH=CH₂ | CH₂-(4-Cl-phenyl) | log p: 6.39 (pH 7.5) |
| I-255 | CH₂CH=CH₂ | CH₂-(3,4-dichlorophenyl) | log p: 6.83 (pH 7.5) |
| I-256 | CH₂CH=CH₂ | CH₂-(4-CF₃-phenyl) | log p: 6.30 (pH 7.5) |
| I-257 | CH₂CH=CH₂ | CH₂-(4-OCF₃-phenyl) | log p: 6.83 (pH 7.5) |
| I-258 | CH₂CH=CH₂ | CH₂CH₂-(4-Cl-phenyl) | |

TABLE 9

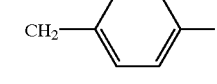

| Ex. No. | R¹ | R² | physical characterization |
|---|---|---|---|
| I-259 | | | |
| I-260 | CH₃ | i-C₃H₇ | |
| I-261 | CH₃ | n-C₄H₉ | |
| I-262 | CH₃ | i-C₄H₉ | |
| I-263 | CH₃ | CH₂CH=CH₂ | |
| I-264 | CH₃ | CH₂C≡CH | |
| I-265 | CH₃ | CH₂-(4-Cl-phenyl) | log p: 6.64 (pH 7.5) |

TABLE 9-continued

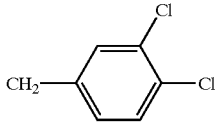

| Ex. No. | R¹ | R² | physical characterization |
|---|---|---|---|
| I-266 | CH₃ | 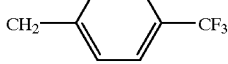 | |
| I-267 | CH₃ |  | |
| I-268 | CH₃ | 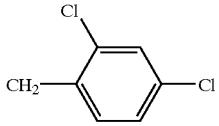 | |
| I-269 | CH₃ | 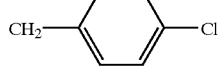 | |

TABLE 10

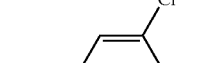

| Ex. No. | R¹ | R² | physical characterization |
|---|---|---|---|
| I-270 | CH₂CH=CH₂ | n-C₃H₇ | |
| I-271 | CH₂CH=CH₂ | i-C₃H₇ | |
| I-272 | CH₂CH=CH₂ | n-C₆H₁₃ | |
| I-273 | CH₂CH=CH₂ | CH₂CH=CH₂ | |
| I-274 | CH₂CH=CH₂ | CH₂C≡CH | |
| I-275 | CH₂CH=CH₂ | 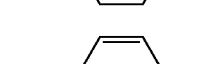 | |
| I-276 | CH₂CH=CH₂ | 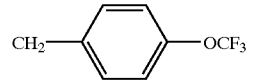 | |
| I-277 | CH₂CH=CH₂ | 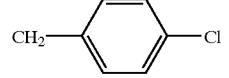 | |

TABLE 10-continued

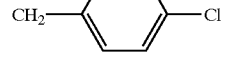

| Ex. No. | R¹ | R² | physical characterization |
|---|---|---|---|
| I-278 | CH₂CH=CH₂ | 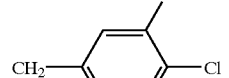 | |
| I-279 | CH₂CH=CH₂ | 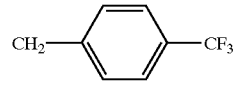 | |
| I-280 | Cl | n-C₃H₇ | |
| I-281 | Cl | i-C₃H₇ | log p: 6.35 (pH 7.5) |
| I-282 | Cl | n-C₆H₁₃ | log p: 7.36 (pH 7.5) |
| I-283 | Cl | CH₂CH=CH₂ | log p: 6.05 (pH 7.5) |
| I-284 | Cl | CH₂C≡CH | log p: 5.37 (pH 7.5) |
| I-285 | Cl | 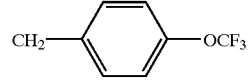 | log p: 6.89 (pH 7.5) |
| I-286 | Cl | 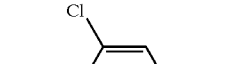 | log p: 7.36 (pH 7.5) |
| I-287 | Cl | (CH₂-C₆H₄-CF₃) | log p: 6.79 (pH 7.5) |
| I-288 | Cl | (CH₂-C₆H₄-OCF₃) | log p: 6.88 (pH 7.5) |
| I-289 | Cl | (CH₂-2,4-Cl₂C₆H₃) | log p: 7.36 (pH 7.5) |

TABLE 11

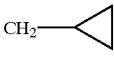

| Ex. No. | R¹ | R² | physical characterization |
|---|---|---|---|
| I-290 | $CH_2CH=CH_2$ | $n\text{-}C_3H_7$ | |
| I-291 | $CH_2CH=CH_2$ | $i\text{-}C_3H_7$ | log p: 6.02 (pH 7.5) |
| I-292 | $CH_2CH=CH_2$ | $n\text{-}C_6H_{13}$ | |
| I-293 | $CH_2CH=CH_2$ | $CH_2CH=CH_2$ | log p: 5.66 (pH 7.5) |
| I-294 | $CH_2CH=CH_2$ | $CH_2C\equiv CH$ | |
| I-295 | $CH_2CH=CH_2$ | 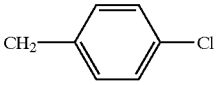 | log p: 5.99 (pH 7.5) |
| I-296 | $CH_2CH=CH_2$ | 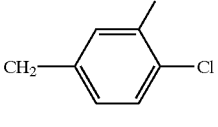 | log p: 6.44 (pH 7.5) |
| I-297 | $CH_2CH=CH_2$ | 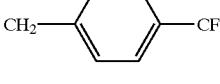 | |
| I-298 | $CH_2CH=CH_2$ | 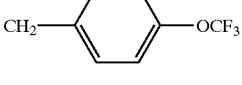 | Mp. 105° C. |
| I-299 | $CH_2CH=CH_2$ | 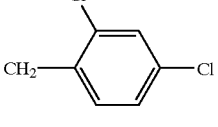 | |
| I-300 | $CH_2CH=CH_2$ | 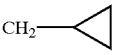 | |
| I-301 | Cl | $n\text{-}C_3H_7$ | Mp. 78–80° C. |
| I-302 | Cl | $i\text{-}C_3H_7$ | log p: 5.42 (pH 7.5) |
| I-303 | Cl | $n\text{-}C_4H_9$ | |
| I-304 | Cl | $CH_2CH=CH_2$ | log p: 5.13 (pH 7.5) |

TABLE 11-continued

| Ex. No. | R¹ | R² | physical characterization |
|---|---|---|---|
| I-305 | Cl | $CH_2C\equiv CH$ | Mp. 112–114° C. |
| I-306 | Cl | 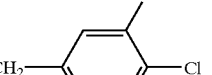 | |
| I-307 | Cl |  | Mp. 108–110° C. |
| I-308 | Cl | 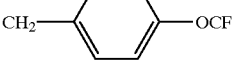 | Mp. 130–32° C. |
| I-309 | Cl |  | Mp. 160–162° C. |
| I-310 | Cl | 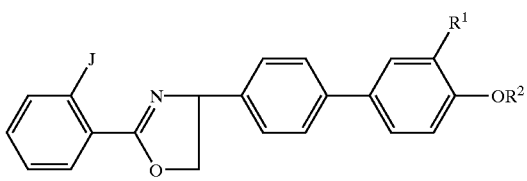 | Mp. 125–127° C. |
| I-311 | Cl | | |

TABLE 12

| Ex. No. | R¹ | R² | physical characterization |
|---|---|---|---|
| I-312 | $CH_2CH_2CH_3$ | $CH_2C\equiv CH$ | Mp. 75–79° C. |

TABLE 12-continued

| Ex. No. | R¹ | R² | physical characterization |
|---|---|---|---|
| I-313 | CH₂CH₂CH₃ | 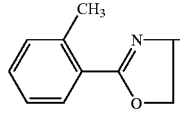 | Mp. 113–115° C. |
| I-314 |  | | log p: 6.44 (pH 7.5) |

*) log p: Logarithm to base ten of the n-octanol/water partition coefficient, determined by reverse phase HPLC analysis using H₂O/CH₃CN.

TABLE 13

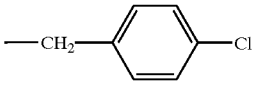

| Ex. No. | X¹ | X² | R¹ | R³ | R² | physical characterization |
|---|---|---|---|---|---|---|
| I-315 | H | Cl | CH₃ | H | 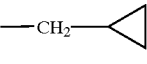 | log p: 6.15 (pH = 7.5) |
| I-316 | H | Br | CH₃ | H | —C₃H₇-i | log p: 5.63 (pH = 7.5) |
| I-317 | H | Cl | CH₃ | H | —CH(CH₃)—CH(OH)CH₃ | log p: 4.08/ 4.13 (pH = 7.5) |
| I-318 | F | F | C₂H₅ | H | 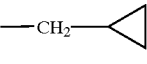 | Mp. 74–75° C. |
| I-319 | F | F | C₂H₅ | H | —CH₂—CH=CH₂ | Mp. 86–88° C. |
| I-320 | F | F | C₂H₅ | H | —CH₂—C≡CH | Mp. 90–92° C. |
| I-321 | F | F | C₂H₅ | H | —CH(CH₃)C₂H₅ | log p: 5.97 (pH = 7.5) |
| I-322 | F | F | C₂H₅ | H | —CH₂—CH(CH₃)₂ | Mp. 70–72° C. |
| I-323 | H | Cl | C₂H₅ | H | —CH₂—CH=CH₂ | Mp. 72–74° C. |
| I-324 | F | F | CH₃ | H | 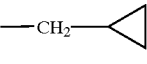 | Mp. 70–72° C. |
| I-325 | F | F | C₂H₅ | H | 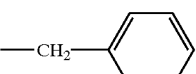 | Mp. 112–15° C. |
| I-326 | H | Cl | C₂H₅ | H | —CH₂—C≡CH | Mp. 78–80° C. |

TABLE 13-continued

[Structure: 2-(2,6-disubstituted phenyl)-4-(biphenyl)oxazoline with R¹, R³ substituents on outer ring and OR² group]

| Ex. No. | X¹ | X² | R¹ | R³ | R² | physical characterization |
|---|---|---|---|---|---|---|
| I-327 | F | F | C₂H₅ | H | —CH₂—(4-CF₃-C₆H₄) | Mp. 112–15° C. |
| I-328 | H | Cl | C₂H₅ | H | —C₃H₇-i | log p: 5.93 (pH = 7.5) |
| I-329 | F | F | Cl | —CH₂—CH=CH₂ | —C₃H₇-i | log p: 5.59 (pH = 7.5) |
| I-330 | F | F | CH₃ | H | —CH₂—(4-C(CH₃)₃-C₆H₄) | Mp. 78–80° C. |
| I-331 | F | F | C₂H₅ | H | —C₄H₉-n | Mp. 88–90° C. |
| I-332 | F | F | C₂H₅ | H | —CH₂—(3,4-Cl₂-C₆H₃) | Mp. 77–79° C. |
| I-333 | H | Br | Cl | —CH₂—CH=CH₂ | —CH₂-cyclopropyl | log p: 6.30 (pH = 7.5) |
| I-334 | H | Br | Cl | —CH₂—CH=CH₂ | —CH₂—(3,4-(CH₃)₂-C₆H₃) | log p: 7.16 (pH = 7.5) |
| I-335 | H | Cl | —CH₂—CH=CH₂ | H | —CH₂-cyclopropyl | log p: 5.96 (pH = 7.5) |
| I-336 | H | Cl | —CH₂—CH=CH₂ | H | —CH₂—C₆H₅ | log p: 5.98 (pH = 7.5) |
| I-337 | H | F | —CH₂—CH=CH₂ | H | —C₃H₇-i | log p: 5.62 (pH = 7.5) |
| I-338 | H | CH₃ | Cl | —CH₂—CH=CH₂ | —C₃H₇-n | log p: 6.93 (pH = 7.5) |
| I-339 | H | CH₃ | Cl | —CH₂—CH=CH₂ | —CH₂—CH=CH₂ | log p: 6.41 (pH = 7.5) |
| I-340 | F | F | C₂H₅ | H | —CH₂—(4-OCF₃-C₆H₄) | Mp. 86–88° C. |
| I-341 | H | Cl | C₂H₅ | H | —CH₂—(4-OCF₃-C₆H₄) | Mp. 78–80° C. |
| I-342 | F | F | Cl | Cl | —CH(CH₃)₂ | log p: 5.65 |

TABLE 13-continued

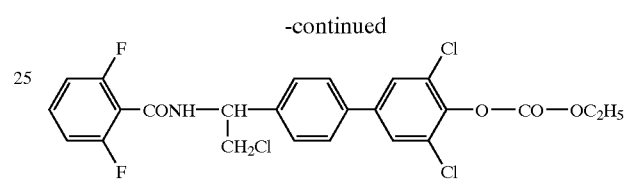

| Ex. No. | $X^1$ | $X^2$ | $R^1$ | $R^3$ | $R^2$ | physical characterization |
|---|---|---|---|---|---|---|
| I-343 | F | F | Cl | Cl | 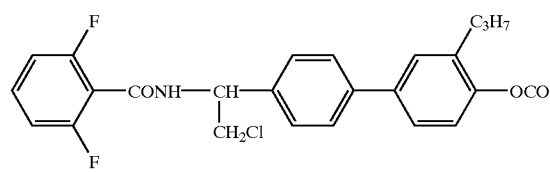 | Mp. 107° C. |
| I-344 | F | F | Cl | Cl | —CH$_2$—CH=CH$_2$ | Mp. 93° C. |
| I-345 | F | F | Cl | Cl | —CF$_3$ | Mp. 80° C. |

Preparation of Starting Materials

Example (VI-1)

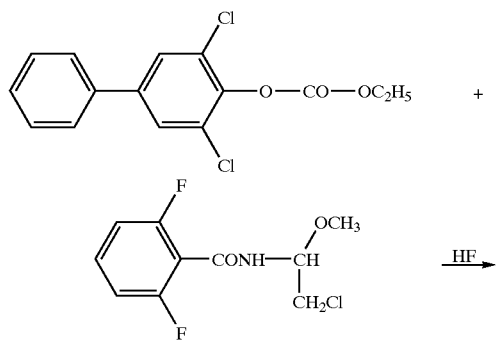

2,6-Difluoro-N-[2-chloro-1-(4-(4-acetoxy-3-n-propylphenyl)phenyl)ethyl]-benzamide At 0° C., 28.5 g (0.215 mol) of aluminium chloride are added a little at a time with stirring to a solution of 14.9 g (59 mmol) of 4-acetoxy-3-n-propylbiphenyl and 16.2 g (65 mmol) of 2,6-difluoro-N-[2-chloro-1-methoxyethyl]-benzamide in 100 ml of dichloromethane. The mixture is stirred for 30 minutes, a further 4 g (30 mmol) of aluminium chloride are added and the mixture is stirred for a further 2 hours at 0° C. The reaction mixture is poured onto ice, the product is extracted with dichloromethane and the organic phase is concentrated under reduced pressure. 27 g of a resinous crude product (log p=3.92, pH 2.3) are obtained and used for further reactions without any further purification (~100% crude yield).

Example (V-2)

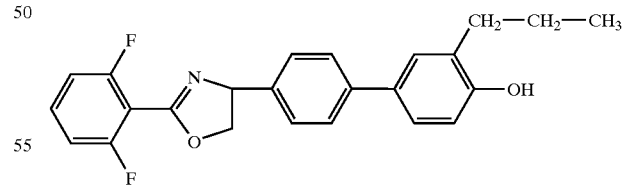

2.6-Difluoro-N-[2-chloro-1-(4-(4-ethoxycarbonyl-3,5-dichlorophenyl)phenyl)ethyl]-benzamide At 0° C., a solution of 32.5 g (0.13 mol) of 2,6-difluoro-N-[2-chloro-1-methoxyethyl]-benzamide and 40 g (0.13 mol) of (2,6-dichloro-4-phenyl)phenylethyl carbonate in 100 ml of dichloromethane are added to 500 ml of hydrofluoric acid. The mixture is stirred overnight at 14° C., the hydrofluoric acid is removed under reduced pressure and the residue is taken up in dichloromethane and washed with water. The organic phase is separated off and concentrated under reduced pressure using a rotary evaporator. 54 g of 2,6-difluoro-N-[2-chloro-1-(4-(4-ethoxycarbonyl-3,5-dichlorophenyl)phenyl)ethyl]-benzamide are obtained as a viscous resin (log p (pH 2.3): 4.17). The product is used for further reactions without any further purification.

Example (II-1)

2-(2,6-Difluorophenyl)-4-(4-(4-hydroxy-3-n-propylphenyl)phenyl)-2-oxazoline

At −10° C., a solution of 3.7 g (92 mmol) of sodium hydroxide in 10 ml of water is added dropwise with stirring to a solution of 27 g (57 mmol) of 2,6-difluoro-N-[2-chloro-1-(4-(4-acetoxy-3-n-propylphenyl)phenyl)ethyl]-benzamide in 150 ml of dimethylformamide. The mixture is stirred overnight, 43 ml of a 25% strength solution of ammonia are added and the mixture is stirred overnight. The reaction mixture is then poured onto ice-water and extracted repeatedly with ethyl acetate. The combined ethyl acetate extracts are dried over MgSO$_4$ and concentrated under reduced pressure.

21 g of crude product (1 g p=3.77, pH=7.5) are obtained (crude yield 93.7%). A small sample of the crude product, stirred with petroleum ether/chloroform, gave a product of Mp. 210–215° C.

Example (II-30)

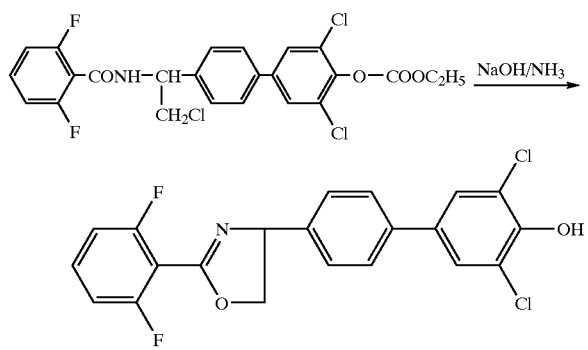

2-(2.6-Difluorophenyl)-4-(4-(4-hydroxy-3,5-dichlorophenyl)phenyl)-4,5-dihydro-oxazoline At 10° C., a solution of 6 g (0.14 mol) of sodium hydroxide in 10 ml of water is added dropwise with stirring to a solution of 53 g (0.1 mol) of 2,6-difluoro-N-[2-chloro-1-(4-(4-ethoxycarbonyl-3,5-dichlorophenyl)phenyl)ethyl]-benzamide in 300 ml of dimethylformamide. The mixture is stirred at 10° C. for 5 h, 100 ml of a 25% strength solution of ammonia are added and the mixture is stirred at 20° C. for 3 days. The reaction mixture is then poured into water and the product is extracted with dichloromethane. The organic phase is removed under reduced pressure and the remaining crude product is stirred with diisopropyl ether. 15 g (yield: 35.8% of theory) of 2-(2,6-difluorophenyl)-4-(4-(4-hydroxy-3,5-dichlorophenyl)phenyl)-4,5-dihydro-oxazoline of Mp. 176–178° C. are obtained.

Similarly, and/or according to the general preparation procedures, the compounds of the formula (II) below are obtained (II)

| Ex. No. | X$^1$ | X$^2$ | R$^1$ | R$^3$ | physical characterization |
|---|---|---|---|---|---|
| II-2 | F | F | CH$_3$ | H | Mp. 186–188° C. |
| II-3 | F | F | CH$_2$CH=CH$_2$ | H | Mp. 210–212° C. |

-continued (II)

| Ex. No. | X$^1$ | X$^2$ | R$^1$ | R$^3$ | physical characterization |
|---|---|---|---|---|---|
| II-4 | H | Br | CH$_3$ | H | Mp. 163–164° C. |
| II-5 | H | Cl | —CH$_2$—CH$_2$—CH$_3$ | H | Mp. 165–166° C. |
| II-6 | H | Br | —CH$_2$—CH$_2$—CH$_3$ | H | Mp. 182–184° C. |
| II-7 | Cl | F | Cl | H | Mp. 166° C. |
| II-8 | Cl | F | —CH$_2$—CH$_2$—CH$_3$ | H | Mp. 210° C. |
| II-9 | H | F | Cl | H | Mp. 138° C. |
| II-10 | Cl | F | CH$_3$ | H | Mp. 190° C. |
| II-11 | H | F | —CH$_2$—CH$_2$—CH$_3$ | H | Mp. 153° C. |
| II-12 | F | F | CH$_3$ | CH$_2$CH=CH$_2$ | log p: 3.83 (pH 7.5) |
| II-13 | F | F | CH$_2$CH=CH$_2$ | CH$_2$CH=CH$_2$ | Mp. 108–10° C. |
| II-14 | H | CH$_3$ | Cl | CH$_2$CH=CH$_2$ | log p: 4.75 (pH 7.5) |
| II-15 | H | CH$_3$ | CH$_3$ | H | |
| II-16 | H | CH$_3$ | Cl | H | Mp. 128–30° C. |
| II-17 | H | Cl | CH$_3$ | H | Mp. 140–43° C. |
| II-18 | H | Cl | CH$_2$CH=CH$_2$ | H | Mp. 85–88° C. |
| II-19 | H | Cl | CH$_3$ | CH$_2$CH=CH$_2$ | log p: 4.14 (pH 7.5) |
| II-20 | H | Br | CH$_2$CH=CH$_2$ | CH$_2$CH=CH$_2$ | |
| II-21 | H | Br | Cl | CH$_2$CH=CH$_2$ | log p: 4.42 (pH 7.5) |
| II-22 | H | Br | Cl | H | Mp. 148–53° C. |
| II-23 | H | CH$_3$ | C$_3$H$_7$-n | H | Mp. 139–41° C. |
| II-24 | F | F | C$_2$H$_5$ | H | log p: 3.42 (pH 7.5) |
| II-25 | H | F | CH$_3$ | H | Mp. 136–38° C. |
| II-26 | F | Cl | —CH$_2$—CH=CH$_2$ | H | Mp. 196° C. |
| II-27 | H | Cl | C$_2$H$_5$ | H | Mp. 152–54° C. |
| II-28 | H | F | —CH$_2$—CH=CH$_2$ | H | Mp. 134° C. |
| II-29 | F | Cl | C$_2$H$_5$ | H | Mp. 193–95° C. |
| II-30 | F | F | Cl | Cl | Mp. 176–178° C. |
| II-31 | F | F | CH$_3$ | CH$_3$ | |

Preparation of 4-acetoxy-3-ethyl-biphenyl

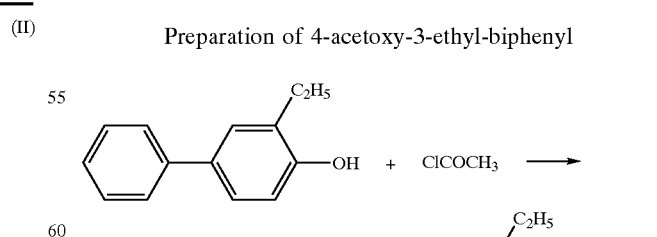

4.6 g (45 mmol) of acetic anhydride are added dropwise to a solution of 7.3 g (37 mmol) of 4-hydroxy-3-ethylbiphenyl and 3.2 g (40 mmol) of pyridine in 60 ml of chloroform, and the mixture is boiled under reflux for 3 hours. The solution is allowed to cool and then washed with water and dilute hydrochloric acid and the organic phase is dried and concentrated. 8.0 g (yield: 90% of theory) of 4-acetoxy-3-ethyl-biphenyl are obtained as a very clear oil of log p=3.92 (pH=2.3).

Preparation of 4-acetoxy-3-propyl-biphenyl

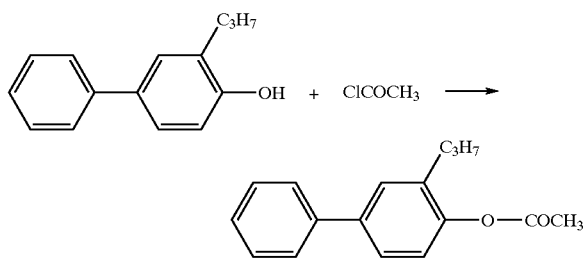

6.1 g (60 mmol) of acetic anhydride are added dropwise to a solution of 10.6 g (50 mmol) of 4-hydroxy-3-propyl-biphenyl, 4.3 g (55 mmol) of pyridine and 0.1 g of 4-(N,N-dimethylamino)pyridine, and the mixture is heated at 50 to 60° C. for 2 hours. The reaction solution is left standing overnight at 20° C. and washed with water and dilute hydrochloric acid, and the organic phase is dried and concentrated. 11.4 g (yield: 89.8% of theory) of 4-acetoxy-3-propyl-biphenyl are obtained as a pale oil of log p=4.32 (pH=2.3).

Preparation of (4-phenyl-2-propyl-phenyl) ethyl carbonate

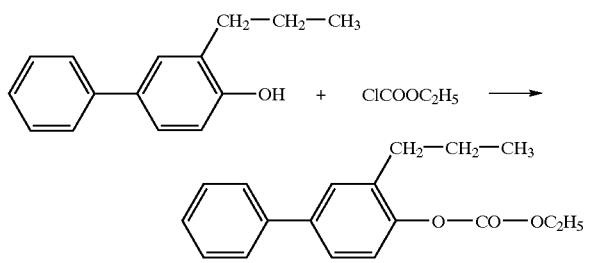

At 5 to 10° C., 18.4 g (0.17 mol) of ethyl chloroformate are added dropwise with cooling to a solution of 36.3 g (0.17 mol) of 4-hydroxy-3-propyl-biphenyl in 160 ml of ethyl acetate and 17.2 g (0.17 mol) of triethylamine. The solution is left standing overnight at 20° C. and washed with water and dilute hydrochloric acid, and the organic phase is dried and concentrated 45 g (yield 93.2% of theory) of (4-phenyl-2-propyl-phenyl) ethyl carbonate are obtained as a pale oil of log p=4.76 (pH=2.3).

Preparation of (2,6-dichloro-4-phenyl)phenyl ethyl carbonate

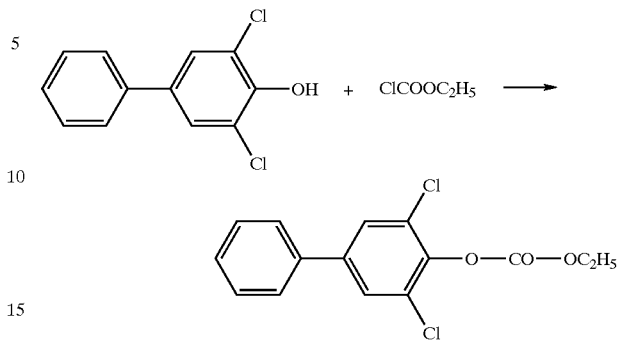

40.6 g (0.17 mol) of 3,5-dichloro-4-hydroxybiphenyl (prepared according to J. C. Colbert et al., JACS 56, 202 (1934)) and 17.2 g (0.17 mol) of triethylamine are dissolved in 170 ml of ethyl acetate and admixed dropwise with 18.4 g (0.17 mol) of ethyl chloroformate at 10° C. The reaction solution is stirred overnight and washed with water, and the organic phase is concentrated. For further purification, the crude product (51.2 g) is chromatographed over silica gel using the system chloroform. 48 g (yield 90.8% of theory) of (2,6-dichloro-4-phenyl-phenyl) ethyl carbonate are obtained as an oil, log p (pH 7.5): 4.65.

Similarly, for example the following compounds are obtained:

(2-Methyl-4-phenyl-phenyl) ethyl carbonate: log p=4.04 (pH=2.3)

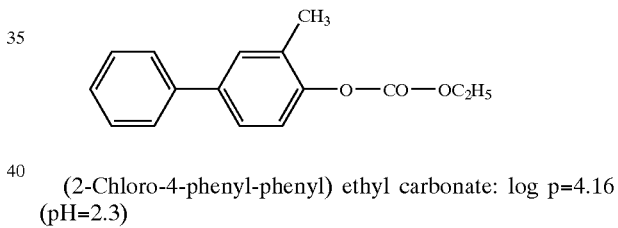

(2-Chloro-4-phenyl-phenyl) ethyl carbonate: log p=4.16 (pH=2.3)

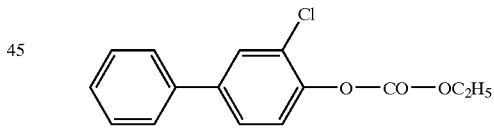

USE EXAMPLES

Example A

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are heavily infested by the green peach aphid (*Myzus persicae*) are treated by being dipped into the active compound preparation of the desired concentration.

After the desired period of time, the kill in % is determined. 100% means that all the aphids have been killed; 0% means that none of the aphids have been killed.

In this test, for example the compounds of Preparation Examples I-19, I-24, I-30 and I-31 effected a kill of in each case at least 90% after 6 days at an exemplary active compound concentration of 0.01%.

Example B
Phaedon Larvae Test

Solvent: 7 parts by weight of dimethylformamide

Emulsifier: 1 part by weight of alkylaryl polyglycol ether

To produce a suitable preparation of active compound, 1 part of weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and populated with larvae of the mustard beetle (*Phaedon cochleariae*) while the leaves are still moist.

After the desired period of time, the kill in % is determined. 100% means that all the beetle larvae have been killed; 0% means that none of the beetle larvae have been killed.

In this test, for example the compounds of Preparation Examples I-2, I-19, I-20, I-30 and I-31 each effected a kill of 100% after 7 days at an exemplary active compound concentration of 0.01%.

The compounds of Preparation Examples I-342, I-343 and I-344 each effected a kill of 100% after 7 days in this test, at an exemplary active compound concentration of 0.1%.

Example C
Spodoptera Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and populated with caterpillars of the owlet moth (*Spodoptera frugiperda*) while the leaves are still moist.

After the desired period of time, the kill in % is determined. 100% means that all the caterpillars have been killed; 0% means that none of the caterpillars have been killed.

In this test, for example the compounds of Preparation Examples I-2, I-19, I-21, I-23, I-25 and I-30 effected a kill of in each case at least 90% after 7 days at an exemplary active compound concentration of 0.0001%.

The compounds of Preparation Examples I-342, I-343 and I-344 effected in each case a kill of 100% after 7 days in this test, at an exemplary active compound concentration of 0.1%.

Example D
Tetranychus Test (OP Resistant/Dip Treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted to the desired concentration using emulsifier-containing water.

Bean plants (*Phaseolus vulgaris*) which are heavily infested by all stages of the greenhouse red spider mite (*Tetranychus urticae*) are dipped into an active compound preparation of the desired concentration.

After the desired period of time, the kill in % is determined. 100% means that all the spider mites have been killed; 0% means that none of the spider mites have been killed.

In this test, for example the compounds of Preparation Examples I-2, I-19, I-21, I-24, I-25, I-27, I-30 and I-31 had an activity of in each case at least 98% after 13 days at an exemplary active compound concentration of 0.0001%.

The compounds of Preparation Examples I-342, I-343 and I-344 effected a kill of 100% after 7 days in this test, at an exemplary active compound concentration of 0.01%.

Example E
Test with Fly Larvae/development-inhibitory Activity

Test animals: All larval stages of *Lucilia cuprina* (OP resistant) [pupae and adults (without contact with the active compound)]

Solvent:
  35 parts by weight of ethylene glycol monomethyl ether
  35 parts by weight of nonylphenol polyglycol ether To prepare a suitable formulation, 3 parts by weight of active compound are mixed with 7 parts of the abovementioned solvent-emulsifier mixture, and the resulting emulsion concentrate is diluted with water to the concentration desired in each case.

For each concentration, 30 to 50 larvae are transferred to horse meat (1 cm$^3$) located in glass tubes, and 500 μl of the test dilution are pipetted onto the meat. The glass tubes are placed into plastic beakers whose bottom is covered with sea sand and kept in a controlled-environment cabinet (26° C. ±1.5° C., 70% ±10% relative humidity). Larvicidal activity is checked after 24 hours and 48 hours. After the larvae have left (about 72 h), the glass tubes are removed and perforated plastic lids are placed on the beakers. After 1½ times the development period (hatching of the control flies), the hatched flies and the pupae/puparia are counted.

The criterion for the activity is the death of the treated larvae after 48 h (larvicidal effect), or inhibition of adults hatching from the pupae or inhibition of pupation. The criterion for the in-vitro activity of a substance is the inhibition of fly development or a standstill of development prior to the adult stage. 100% larvicidal activity means that all the larvae have died after 48 hours. 100% development-inhibitory activity means that no adult flies have hatched.

In this test, for example the compounds of Preparation Examples I-19, I-20, I-22 and I-23 exhibited a development-inhibitory activity of in each case 100% at an exemplary concentration of 100 ppm.

Example F
*Spodoptera exigua* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and populated with caterpillars of the army worm (*Spodoptera exigua*) while the leaves are still moist.

After the desired period of time, the activity in % is determined. 100% means that all the caterpillars have been killed; 0% means that none of the caterpillars have been killed.

In this test, for example the compound of Preparation Example I-342 effected a kill of 100% after 6 days, at an exemplary active compound concentration of 0.1%.

Example G

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and populated with caterpillars of the diamond back moth (*Plutella xylostella*) while the leaves are still moist.

After the desired period of time, the kill in % is determined. 100% means that all the caterpillars have been killed; 0% means that none of the caterpillars have been killed.

In this test, for example the compound of Preparation Example I-342 effected a kill of 100% after 6 days, at an exemplary active compound concentration of 0.1%.

Example H

Nephotettix Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the active compound preparation of the desired concentration and populated with green rice leaf hoppers (*Nephotettix cincticeps*) while the seedlings are still moist.

After the desired period of time, the kill in % is determined. 100% means that all the leaf hoppers have been killed; 0% means that none of the leaf hoppers have been killed.

In this test, for example the compounds of Preparation Examples I-343 and I-344 effected a kill of 100% after 6 days, at an exemplary active compound concentration of 1%.

Example I

*Heliothis armigera* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Soya bean shoots (*Glycine max*) are treated by being dipped into the active compound preparation of the desired concentration and populated with caterpillars of the cotton bollworm (*Heliothis armigera*) while the leaves are still moist.

After the desired period of time, the kill in % is determined. 100% means that all the caterpillars have been killed; 0% means that none of the caterpillars have been killed.

In this test, for example the compound of Preparation Example I-342 effected a kill of 100% in 6 days, at an exemplary active compound concentration of 0.1%.

What is claimed is:

1. A compound of the Formula (I)

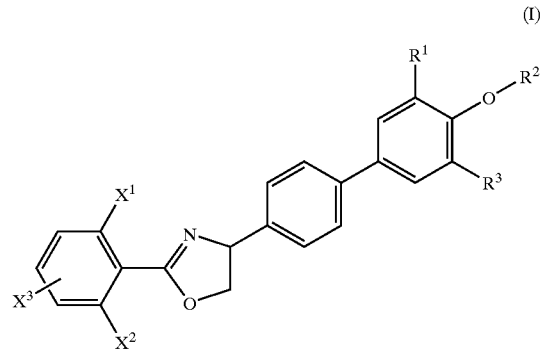

wherein

X1 represents hydrogen, fluorine, chlorine, bromine, iodine, $C_1-C_6$-alkyl, $C_1-C_6$-alkoxy or $C_1-C_6$-alkylthio, X2 represents fluorine, chlorine, bromine, iodine, $C_1-C_6$-alkyl, $C_1-C_6$-alkoxy or $C_1-C_6$-alkylthio, X3 represents hydrogen, fluorine, chlorine, $C_1-C_6$-alkyl or $C_1-C_6$-alkoxy, R1 represents hydrogen, fluorine, chlorine, bromine, $C_1-C_6$-alkyl or —$CH_2$—$CR4$=$CH_2$, R2 represents $C_1-C_8$-alkyl, $C_1-C_6$-hydroxyalkyl, $C_3-C_{10}$-alkenyl, $C_3-C_{12}$-alkinyl, or represents unsubstituted or halogen- or $C_1-C_4$-alkyl-substituted $C_3-C_6$-cycloalkyl or $C_4-C_6$-cycloalkenyl, or represents unsubstituted or halogen-, $C_1-C_4$-alkyl-, $C_2-C_4$-alkenyl-, $C_2-C_4$-halogenoalkenyl-, phenyl-, halogenophenyl-, styryl- or halogenostyryl-substituted $C_3-C_6$-cycloalkyl-$C_1-C_4$-alkyl, or represents unsubstituted or halogen- or $C_1-C_4$-alkyl-substituted $C_4-C_8$-cycloalkenyl-$C_1-C_2$-alkyl, or represents phenyl-$C_1-C_4$-alkyl which is unsubstituted or mono- to tetrasubstituted by identical or different substituents from the group consisting of nitro, halogen, $C_1-C_{12}$-alkyl, $C_1-C_{12}$-halogenoalkyl, $C_1-C_{12}$-alkylthio, $C_1-C_{12}$-halogenoalkylthio, $C_1-C_{12}$-alkoxy and $C_1-C_{12}$-halogenoalkoxy, or represents naphthyl-$C_1-C_3$-alkyl or tetrahydronaphthyl-$C_1-C_3$-alkyl, R3 represents hydrogen, $C_1-C_4$-alkyl, fluorine, chlorine, bromine or represents —$CH_2$—$CR4$=$CH_2$, wherein R1 and R3 do not simultaneously represent hydrogen, and R4 represents hydrogen, $C_1-C_{12}$-alkyl or represents phenyl which is unsubstituted or mono- to tetrasubstituted by identical or different substituents from the group consisting of halogen, $C_1-C_{12}$-alkyl, $C_1-C_{12}$-halogenoalkyl, $C_1-C_{12}$-alkoxy and $C_1-C_{12}$-halogenoalkoxy.

2. A compound of the Formula (I) of claim 1 wherein $X^1$ represents hydrogen, fluorine or chlorine, $X^2$ represents fluorine, chlorine, bromine, iodine, $C_1-C_3$-alkyl or $C_1-C_3$-alkoxy, $X^3$ represents hydrogen, fluorine, chlorine, $C_1-C_3$-alkyl or $C_1-C_3$-alkoxy, $R^1$ represents hydrogen, fluorine, chlorine, bromine, $C_1-C_4$-alkyl or —$CH_2$—$CR^4$=$CH_2$, $R^2$ represents $C_1-C_6$-alkyl, $C_1-C_4$-hydroxyalkyl, $C_3-C_{10}$-alkenyl, $C_3-C_5$-alkinyl, or represents unsubstituted or halogen- or $C_1-C_4$-alkyl-substituted cyclohexyl or $C_4-C_6$-cycloalkenyl, or represents unsubstituted or halogen-, $C_1$–$C_4$-alkyl-, $C_2$–$C_4$-alkenyl-, $C_2$–$C_3$-halogenoalkenyl-, phenyl-, halogenophenyl-, styryl- or halogenostyryl-substituted $C_3$–$C_6$-cycloalkyl-$C_1$–$C_4$-alkyl, or represents unsubstituted or halogen-substituted $C_4$–$C_6$-cycloalkenylmethyl or represents benzyl which is unsubstituted or mono- or disubstituted by identical or different substituents from the group consisting of nitro, halogen, $C_1$–$C_4$-alkyl, $C_1$–$C_4$-halogenoalkyl, $C_1$–$C_4$-alkylthio, $C_1$–$C_4$-halogenoalkylthio, $C_1$–$C_4$-alkoxy and $C_1$–$C_4$-halogenoalkoxy, or represents naphthylmethyl or tetrahydronaphthylmethyl, $R^3$ represents hydrogen, $C_1$–$C_3$-alkyl, chlorine, bromine or —$CH_2$—$CR^4$=$CH_2$, wherein $R^1$ and $R^3$ do not simultaneously represent hydrogen, and $R^4$ represents hydrogen, $C_1$–$C_4$-alkyl or represents phenyl which is unsubstituted or mono- or disubstituted by identical or different substituents from the group consisting of fluorine, chlorine, bromine, $C_1$–$C_4$-alkyl, $C_1$–$C_4$-halogenoalkyl and $C_1$–$C_4$-halogenoalkoxy.

3. A compound of the Formula (I) of claim 1 wherein $X^1$ represents hydrogen, fluorine or chlorine, $X^2$ represents fluorine, chlorine, bromine, iodine, methyl or methoxy, $X^3$ represents hydrogen, fluorine, chlorine or methyl, $R^1$ represents hydrogen, fluorine, chlorine, bromine, methyl, ethyl, n- or i-propyl or represents allyl, $R^2$ represents methyl, ethyl, n- or i-propyl, n-butyl, i-butyl, s-butyl, n-pentyl, n-hexyl, hydroxyethyl, hydroxypropyl, hydroxybutyl, or represents —$CH_2$—CH=$CH_2$, —$CH_2$—C($CH_3$)=$CH_2$, —$CH_2$—C≡CH or —CH($CH_3$)C≡CH, or represents a cycloalkylalkyl selected from the group consisting of the following cycloalkylalkyl groupings:

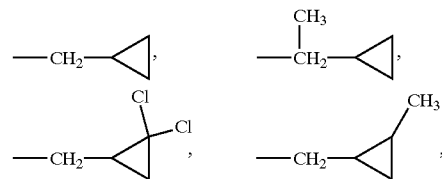
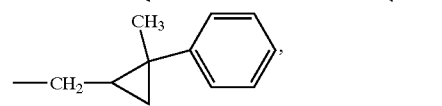
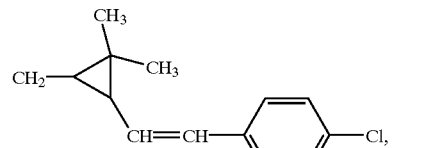
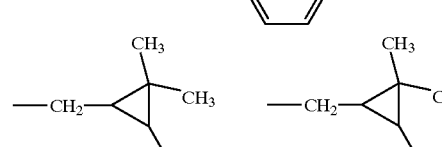
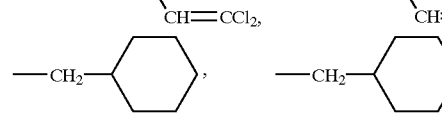

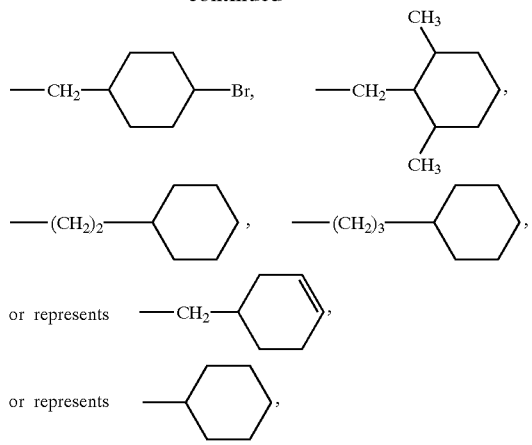

or represents a radical selected from the group consisting of the following radicals

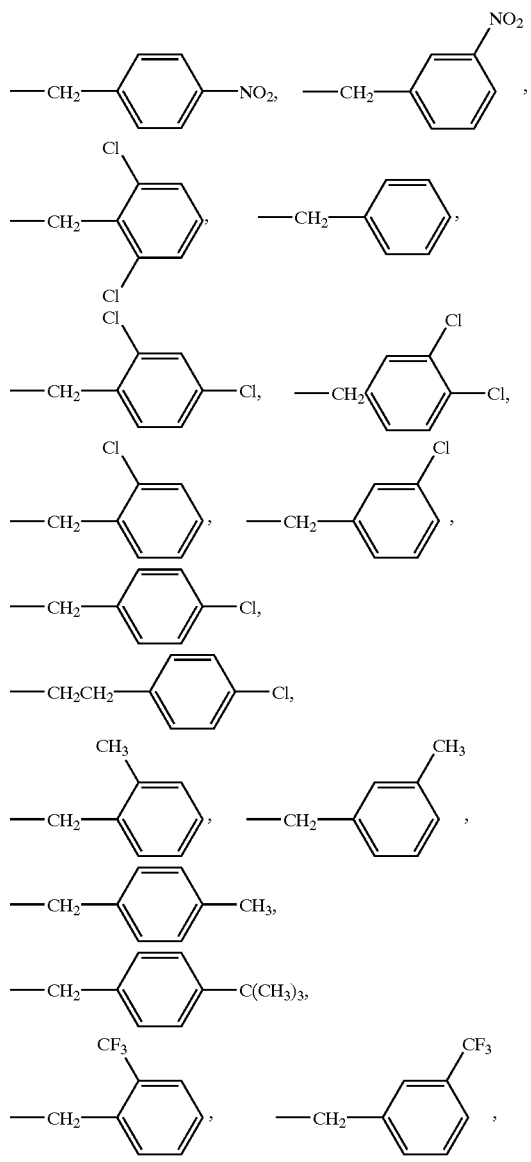

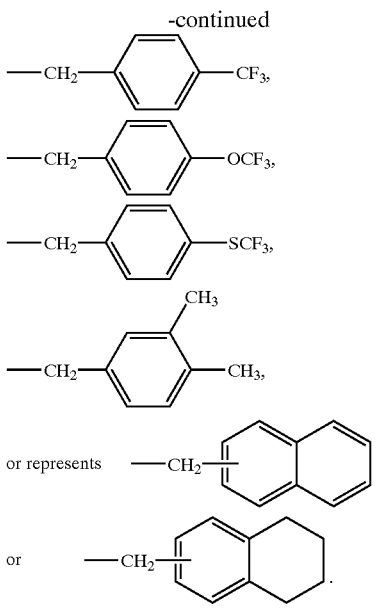

and

R³ represents hydrogen, chlorine, bromine, methyl or —CH₂—CH=CH₂, wherein R¹ and R³ do not simultaneously represent hydrogen.

4. A compound of the Formula (Ia)

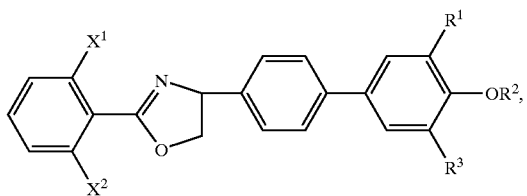

wherein $R^1$, $R^2$, $R^3$, $X^1$ and $X^2$ are each as defined in claim 1.

5. A compound of the Formula (Ib)

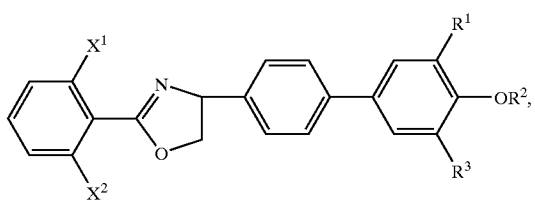

wherein $X^1$ represents hydrogen or fluorine, $X^2$ represents fluorine, chlorine, bromine or methyl, $R^1$ represents chlorine, methyl, ethyl, n- or i-propyl or allyl, $R^2$ is as defined in claim 1, and $R^3$ is as defined in claim 1.

6. A pesticide, for controlling pests selected from the group consisting of insects, arachnids and nematodes, comprising an effective amount of one or more compounds of the formula (I) according to claim 1 and a member selected from the group consisting of an extender, a solid carrier, a surfactant and combinations thereof.

7. A method for controlling pests selected from the group consisting of insects, arachnids and nematodes, comprising the step of allowing an effective amount of a compound of the Formula (I) according to claim 1 to act on a member selected from the group consisting of said pests, a habitat of said pests and combinations thereof.

8. A process for preparing a compound of the Formula (I) of claim 1 comprising the step of reacting a compound of the Formula (II)

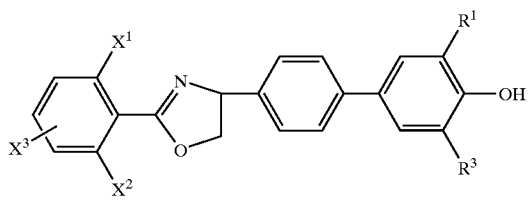

wherein $X^1$, $X^2$, $X^3$, $R^1$ and $R^3$ are each as defined in claim 1, with a compound of the formula (III)

$$Z—R^2 \qquad (III)$$

wherein $R^2$ is as defined in claim 1 and

Z represents a leaving group selected from the group consisting of halogen, alkylsulphonyloxy and arylsulphonlyoxy.

9. The process of claim 8 wherein said reaction is carried out in the presence of a diluent.

10. The process of claim 8 wherein said reaction is carried out in the presence of a base.

11. The process of claim 8 wherein said reaction is carried out in the presence of a diluent and base.

12. The process of claim 8 wherein Z represents a leaving group, said leaving group being selected from the group consisting of chlorine, bromine, methylsulphonyloxy, phenylsulphonyloxy, p-chlorophenylsulphonyloxy and tolylsulphonyloxy.

* * * * *